(12) United States Patent
Gobbi et al.

(10) Patent No.: US 8,097,637 B2
(45) Date of Patent: *Jan. 17, 2012

(54) BENZOYL-PIPERIDINE DERIVATIVES AS DUAL MODULATORS OF THE 5-HT2A AND D3 RECEPTORS

(75) Inventors: Luca Gobbi, Oberwil BL (CH); Georg Jaeschke, Basel (CH); Rosa Maria Rodriguez Sarmiento, Basel (CH); Lucinda Steward, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 653 days.

This patent is subject to a terminal disclaimer.

(21) Appl. No.: 12/184,272

(22) Filed: Aug. 1, 2008

(65) Prior Publication Data

US 2009/0042943 A1 Feb. 12, 2009

(30) Foreign Application Priority Data

Aug. 9, 2007 (EP) .................................... 07114119

(51) Int. Cl.
*A61K 31/445* (2006.01)
*C07D 211/32* (2006.01)

(52) U.S. Cl. ................ 514/330; 514/253.13; 514/235.2; 514/303; 514/314; 514/317; 514/321; 514/323; 514/326; 544/129; 544/360; 546/118; 546/176; 546/194; 546/198; 546/210; 546/225

(58) Field of Classification Search ............. 514/253.13, 514/235.2, 303, 314, 317, 318, 321, 323, 514/326, 330; 544/129, 360; 546/118, 176, 546/194, 198, 201, 210, 225
See application file for complete search history.

(56) References Cited

FOREIGN PATENT DOCUMENTS

| WO | WO 03/028725 | 4/2003 |
| WO | WO 2007/093540 | 8/2007 |

OTHER PUBLICATIONS

Gobbi et al. "Benzoyl-piperidine . . . " Ca147:300997(2007).*
Ravina et al. "conformationally constrain . . . " J. Med. Chem. 42, p. 2274-2797 (1999).*
Patani et al. "Bioisosterism: a rational . . . " Chem. Rev. 96 p. 3147-3176 (1996).*
Roth et al., Nat. Rev. Drug. Discovery vol. 3 pp. 353-359 (2004).
Lieberman et al., N. Engl. J. Med. vol. 353, pp. 1209-1223 (2005).
Missale et al., Physiol. Rev. vol. 78 pp. 189-225 (1998).
Gurevich E.V., Neuropsychopharmacology vol. 20 pp. 60-80 (1999).
Joyce J. N., Drug Discovery Today 1, vol. 10, No. 13 pp. 917-925 (2005).
Gurevich E.V., Arch. Gen. Psychiatry vol. 54 pp. 225-232 (1997).
Leikin et al., Med. Toxicol. Adverse Drug Exp. vol. 4 pp. 324-350 (1989).
Harrison P. J., Br. J. Psychiatry Suppl. 38 pp. 12-22 (1999).
Barnes N. M., Neuropharmacology vol. 38 pp. 1083-1152 (1999).
Pompeiano et al., Brain Res. Mol. vol. 23 pp. 163-178 (1994).
Pazos et al., Neuroscience vol. 21 pp. 123-139 (1987).
Roth et al., Pharmacol. Ther. vol. 79 pp. 231-257 (1998).
Spurlock et al., Mol. Psychiatry vol. 3 pp. 42-49 (1998).
Arranz et al., Lancet vol. 355 pp. 1615-1616 (2000).
Porras et al., Neuropsychopharmacology vol. 26 pp. 311-324 (2002).
De Angelis L., Curr. Opin. Investig. Drugs. vol. 3 pp. 106-112 (2002).
Meltzer et al., J. Pharmacol. Exp. Ther. vol. 251 pp. 238-246 (1989).
Wustrow et al., Journal of Medicinal Chemistry vol. 41 pp. 760-771 (1998).
Reaville, et al., JPET vol. 294 pp. 1154-1165 (2000).
Vorel et al., J. Neurosci. vol. 22 pp. 9595-9603 (2002).
Campos et al. Soc. Neurosci. Abstr. pp. 322-328 (2003).
Ashby et al., Synapse vol. 48 pp. 154-156 (2003).
Drescher et al., Am. Soc. Neurosci. pp. 894-896 (2002).
Ungnade et al., Literature Journal of the American Chem. Society vol. 70 pp. 1898-1899 (1948).
Peters et al., Tetrahedron vol. 38(24) pp. 3641-3647 (1982).
Jenny et al., Helvetica Chimica Acta vol. 75 p. 1945 and 1950 (1992).
Chilean Office Action in Corres. Appl. CL 2310-2008 dated May 12, 2011.

* cited by examiner

*Primary Examiner* — Celia Chang
(74) *Attorney, Agent, or Firm* — George W. Johnston; Patricia S. Rocha-Tramaloni; Kimberly J. Prior

(57) ABSTRACT

The present invention relates to compounds of formula (I)

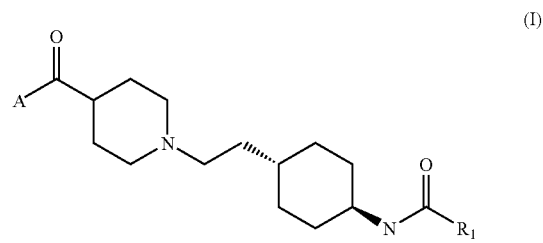

(I)

wherein $R_1$ and A are as defined in the specification as dual modulators of the serotonin $5\text{-HT}_{2a}$ and dopamine $D_3$ receptors, their manufacture, pharmaceutical compositions containing them and their use as medicaments. Compounds of general formula (I) have high affinity for the dopamine $D_3$ and serotonin (5-Hydroxytryptamine; 5-HT) $5\text{-HT}_{2A}$ receptors and are effective in the treatment of psychotic disorders, as well as other diseases such as depression and anxiety, drug dependence, dementias and memory impairment.

15 Claims, No Drawings

BENZOYL-PIPERIDINE DERIVATIVES AS DUAL MODULATORS OF THE 5-HT2A AND D3 RECEPTORS

PRIORITY TO RELATED APPLICATION(S)

This application claims the benefit of European Patent Application No. 07114119.6, filed Aug. 9, 2007, which is hereby incorporated by reference in its entirety.

BACKGROUND OF THE INVENTION

Schizophrenia is characterized by complex symptomatology including positive symptoms, (i.e. delusions and hallucinations), and negative symptoms, (i.e. anhedonia, restricted fluency and productivity of thought and speech). In addition it is now well recognized that cognitive impairment is the third major diagnostic category of schizophrenia, characterized by loss in working memory as well as other deficits. Other symptoms include aggressiveness, depression and anxiety (Stahl, S. M. (2000) Essential Psychopharmacology. Neuroscientific Basis and Practical Applications. Cambridge University Press, second edition, Cambridge, UK). The different categories and the clinical features of the disorder are defined in diagnostic schemes such as DSM-IV (Diagnostic and statistical manual of mental disorders, $4^{th}$ edition) or ICD-10 (International classification of diseases, $10^{th}$ edition). Currently used medications to treat schizophrenia, bipolar mania and other psychoses, include antipsychotics both typical ($D_2/D_3$ preferring) or the more recent atypicals, which exhibit polypharmacology interacting at multiple receptors (eg., $D_1$, $D_2$, $D_3$, $D_4$, $5-HT_{1A}$, $5-HT_{2A}$, $5-HT_{2C}$, $H_1$, $M_1$, $M_2$, $M_4$, etc; Roth, B. L. et al. (2004) Magic shotguns versus magic bullets: selectively non-selective drugs for mood disorders and schizophrenia. Nat. Rev. Drug Discov. 3, 353-359). These antipsychotics, although relatively successful (some patients exhibit treatment resistance) at treating the positive symptoms of schizophrenia, are less effective at treating negative symptoms, cognitive deficits, and associated depression and anxiety, all of which lead to reduced patient quality of life and socioeconomic problems (Lieberman, J. A. et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223). Furthermore, patient compliance is compromised by prevalent side effects such as weight gain, extrapyramidal symptoms (EPS), and cardiovascular effects (Lieberman, J. A. et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223). In the current invention, compounds with high affinity and greater selectivity for $D_3$ and $5-HT_{2A}$ receptors are described and are proposed to treat psychoses and other diseases, with fewer associated side affects.

Dopamine, a major catecholamine neurotransmitter, is involved in the regulation of a variety of functions which include emotion, cognition, motor functions, and positive reinforcement, (Purves, D. et al. (2004) Neuroscience. Sinauer, third edition, Sunderland, Mass.). The biological activities of dopamine are mediated through G protein-coupled receptors (GPCRs) and in human, five different dopamine receptors $D_1$-$D_5$ have been identified, where the $D_2$-like receptors ($D_2$, $D_3$ and $D_4$) couple to the G-protein $G_{\alpha I}$ (Missale, C. et al. (1998) Dopamine receptors: from structure to function. Physiol. Rev. 78, 189-225). The $D_3$ dopamine receptor is most highly expressed in the nucleus accumbens (Gurevich, E. V., Joyce, J. N. (1999) Distribution of dopamine D3 receptor expressing neurons in the human forebrain: comparison with D2 receptor expressing neurons. Neuropsychopharmacology 20, 60-80), and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei. The limbic circuit is thought to be important for emotional behavior and thus $D_3$ receptor antagonists are proposed to modulate psychotic symptoms such as hallucinations, delusions and thought disorder (Joyce, J. N. and Millan, M. J., (2005) Dopamine D3 receptor antagonists as therapeutic agents. Drug Discovery Today, 1 July, Vol. 10, No. 13, 917-25), while these antagonists spare the $D_2$ modulated striatal extrapyramidal system (associated with EPS induction). In addition, it has been reported that drug naive schizophrenic patients show altered levels of $D_3$ receptor expression (Gurevich, E. V. et al. (1997) Mesolimbic dopamine D3 receptors and use of antipsychotics in patients with schizophrenia. A postmortem study. Arch. Gen. Psychiatry 54, 225-232) and dopamine release (Laruelle, M. (2000) Imaging dopamine dysregulation in schizophrenia: implication for treatment. Presented at Workshop Schizophr: Pathol. Bases and Mech. Antipsychotic Action, Chicago), indicating that a disturbed homeostasis of dopamine plays an important role in the etiology of schizophrenic symptoms.

The neurotransmitter serotonin is implicated in several psychiatric conditions including schizophrenia (Kandel, E. R. et al. (eds.; 2000) Principles of Neural Science, $3^{rd}$ edition Appleton & Lange, Norwalk, Conn.). The involvement of serotonin in psychotic disorders is suggested by multiple studies which include treatment in humans with the psychotropic drug Lysergic acid (LSD; a serotonin agonist) which can induce schizophrenia-like symptoms such as hallucinations (Leikin, J. B. et al. (1989) Clinical features and management of intoxication due to hallucinogenic drugs. Med. Toxicol. Adverse Drug Exp. 4, 324-350). Furthermore, altered brain distribution of serotonin receptors as well as an altered serotonergic tone, have been detected in schizophrenic patients (Harrison, P. J. (1999) Neurochemical alterations in schizophrenia affecting the putative receptor targets of atypical antipsychotics. Focus on dopamine (D1, D3, D4) and 5-HT2A receptors. Br. J. Psychiatry Suppl. 38, 12-22). In mammals serotonin exerts its biological activities through a family of 14 5-HT GPCRs (Barnes, N. M., Sharp, T. (1999) A review of central 5-HT receptors and their function. Neuropharmacology 38, 1083-1152). The $5-HT_{2A}$ receptor is most prominently expressed in the prefrontal cortex and at lower levels in the basal ganglia and the hippocampus in human brain (Pompeiano, M. et al. (1994) Distribution of the serotonin 5-HT2 receptor family mRNAs: comparison between 5-HT2A and 5-HT2C receptors. Brain Res. Mol. Brain Res. 23, 163-178; Pazos, A., Probst, A., Palacios, J. M. (1987) Serotonin receptors in the human brain—IV. Autoradiographic mapping of serotonin-2 receptors. Neuroscience 21, 123-139), and is coupled predominantly to the G-protein $G_{\alpha q}$ (Roth, B. L. et al. (1998) 5-Hydroxytryptamine2-family receptors (5-hydroxytryptamine2A, 5-hydroxytryptamine2B, 5-hydroxytryptamine2C): where structure meets function. Pharmacol. Ther. 79, 231-257). Genetic linkage studies of a $5-HT_{2A}$ polymorphism to schizophrenia (Spurlock, G. et al. (1998) A family based association study of T102C polymorphism in 5HT2A and schizophrenia plus identification of new polymorphisms in the promoter. Mol. Psychiatry 3, 42-49), as well as responsiveness to antipsychotic drugs (Arranz, M. J. et al. (2000) Pharmacogenetic prediction of clozapine response. Lancet 355, 1615-1616), further suggests a role for the $5-HT_{2A}$ receptor both in the treatment and pathology of psychosis. In addition, dopaminergic neurotransmission appears to be under the afferent regulation of the $5-HT_{2A}$ receptor (Porras, G. et al. 5-HT2A and 5-HT2C/2B receptor subtypes modulate dopamine release induced in vivo by amphetamine and morphine in both the rat nucleus accumbens and striatum. Neuropsychopharmacology 26, 311-324-2002). Overall $5-HT_{2A}$ receptor antagonists are proposed to be suitable for the treatment of disorders

SUMMARY OF THE INVENTION

In particular, the present invention provides compounds of formula (I)

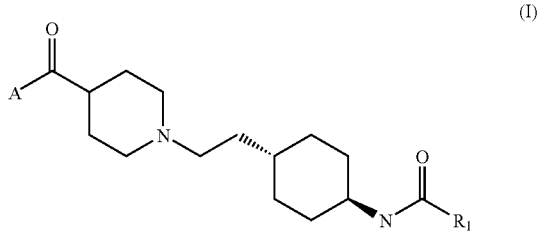

wherein
R₁:

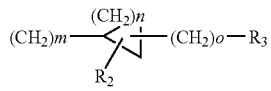

A is aryl or 5 to 6 membered heteroaryl, each of which is optionally substituted by one to five substituents selected from the group consisting of cyano, halo, $C_{1-6}$-alkyl, $C_{1-6}$-haloalkyl and $C_{1-6}$-alkoxy;
m is 1, 2 or 3;
n is 1, 2, 3, 4 or 5;
o is 0, 1 or 2;
R₂ is selected from the group consisting of hydrogen, hydroxyl, $C_{1-6}$-alkyl, $C_{1-6}$-haloalkyl and $C_{1-6}$-alkoxy; and
R₃ is selected from the group consisting of
  hydrogen, provided that R² ≠ hydrogen;
  hydroxyl;
  $C_{1-6}$-alkyl;
  $C_{1-6}$-haloalkyl;
  $C_{1-6}$-haloalkoxy;
  oxo;
  —NH(CO)—$C_{1-6}$-alkyl;
  —O—$C_{1-6}$-alkyl;
  —O—$C_{3-7}$-cycloalkyl; and
  —O-(3 to 7 membered heterocycloalkyl);
as well as pharmaceutically acceptable salts thereof.

Compounds of formula (I) according to the invention are very effective dual modulators of the serotonin 5-HT$_{2a}$ and dopamine D₃ receptors.

The compounds of the invention have high affinity for the dopamine D₃ and serotonin (5-Hydroxytryptamine; 5-HT) 5-HT$_{2A}$ receptors and are believed to be effective in the treatment of psychotic disorders, as well as other diseases such as depression and anxiety, drug dependence, dementias and memory impairment. Psychotic disorders encompass a variety of diseases, which include schizophrenia, schizoaffective disorders, bipolar disease, mania, psychotic depression, and other psychoses involving paranoia and delusions.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

"Aryl" represents an aromatic carbocyclic group consisting of one individual ring, or one or more fused rings in which at least one ring is aromatic in nature. A preferred aryl group is phenyl or naphthyl, as well as those specifically illustrated by the examples herein below.

"$C_{1-6}$-alkyl" denotes a straight- or branched-carbon chain group containing from 1 to 6 carbon atoms, for example, methyl, ethyl, propyl, isopropyl, isobutyl, sec-butyl, tert-butyl, pentyl, n-hexyl as well as those specifically illustrated by the examples herein below.

"Halo" or "Halogen" denotes chlorine, iodine, fluorine and bromine.

"$C_{1-6}$-haloalkyl" denotes a $C_{1-6}$-alkyl group as defined above which is substituted by one or more halogen atom. Examples of $C_{1-6}$-haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_1$-$C_7$-haloalkyl are difluoro- or trifluoro-methyl or ethyl.

"$C_{1-6}$-alkoxy" denotes an alkyl group as defined above that is connected via an oxygen atom.

"$C_{1-6}$-haloalkoxy" denotes a $C_{1-6}$-alkoxy group as defined above which is substituted by one or more halogen atom. Examples of $C_{1-6}$-haloalkoxy include but are not limited to methoxy or ethoxy, substituted by one or more Cl, F, Br or I atom(s) as well as those groups specifically illustrated by the examples herein below. Preferred $C_1$-$C_7$ haloalkoxy are difluoro- or trifluoro-methoxy or ethoxy.

"$C_{3-7}$-cycloalkyl" denotes a monovalent saturated carbocyclic moiety, consisting of one, two or three carbon rings having 3 to 7 carbon atoms as ring members and includes but is not limited to cyclopropyl, cyclobutyl, cyclopentyl, cyclohexyl, and cycloheptyl as well as those groups specifically illustrated by the examples herein below.

"5 to 6 membered heteroaryl" means a monocyclic aromatic ring having 5 to 6 ring atoms wherein one, two, or three ring atoms are heteroatoms selected from N, O, and S, the remaining ring atoms being C. Heteroaryl can optionally be substituted with one, two, three or four substituents, wherein each substituent is independently hydroxy, cyano, alkyl, alkoxy, thioalkyl, halo, haloalkyl, hydroxyalkyl, alkoxycarbonyl, amino, acetyl, —NHCOOC(CH₃)₃ or halogen substituted benzyl. "5 to 6 membered heteroaryl" includes bicyclic and tricyclic moieties in which one of the fused rings is a monocyclic aromatic ring as defined above and the other rings are carbocyclic, heterocyclic, aromatic, or heteroaryl. The non aromatic part of the ring system also can be substituted by oxo, unless otherwise specifically indicated. Examples of heteroaryl moieties include, but are not limited to, optionally substituted imidazolyl, optionally substituted thiophenyl, optionally substituted oxazolyl, optionally substituted isoxazolyl, optionally substituted thiazolyl, optionally substituted pyrazinyl, optionally substituted pyrrolyl, optionally substituted pyridinyl, optionally substituted pyrimidinyl, optionally substituted pyridazinyl, optionally substituted indolyl, optionally substituted isoindolyl, optionally substituted 2,3-dihydroinidolyl, optionally substituted indazolyl, optionally substituted naphthyridinyl, optionally substituted isoquinolinyl, optionally substituted carbazol-9-yl, optionally substituted furanyl, optionally substituted benzofuranyl, optionally substituted quinolinyl, optionally substituted benzo[1,3]dioxolyl, optionally substituted benzo[1,2,3]thiadiazolyl, optionally substituted benzo[b]thiophenyl, optionally substituted 9H-thioxanthenyl, optionally substituted thieno[2,3-c]pyridinyl, optionally substituted 3H-imidazo[4,5,b]pyridinyl, optionally substituted phthalazinyl, optionally substituted 2,3-dihydrobenzo[1,4]dioxinyl, and the like or those which are specifically exemplified herein.

"3 to 7 membered heterocycloalkyl" means a monovalent saturated moiety, consisting of one, two or three rings, incorporating one, two, or three ring heteroatoms (chosen from nitrogen, oxygen or sulfur). Heterocycloalkyl can optionally be substituted with one, two, three or four substituents, wherein each substituent is independently hydroxy, alkyl, alkoxy, thioalkyl, halo, haloalkyl, hydroxyalkyl, alkoxycarbonyl, amino, alkylamino, dialkylamino, aminocarbonyl, or carbonylamino, unless otherwise specifically indicated. Preferred 3 to 7 membered heterocycloalkyls are 5 or 6 membered heterocycloalkyls.

"Thiophenyl" is synonymous with "thienyl" and denotes a thiophene substituent, i.e., $C_4H_4S$.

"One or more" denotes herein, 1, 2, 3, 4, 5, 6, 7, 8, 9 or 10 and preferably 1, 2, 3, 4 or 5 and still more preferably 1, 2 or 3.

"Oxo" denotes a group =O.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like.

"Therapeutically effective amount" means an amount that is effective to prevent, alleviate or ameliorate symptoms of disease or prolong the survival of the subject being treated.

The present invention provides compounds of formula (I)

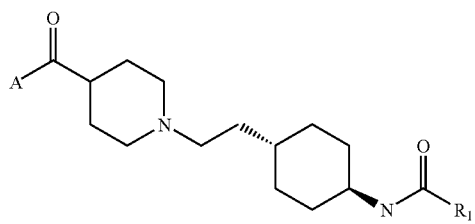

(I)

wherein
$R_1$:

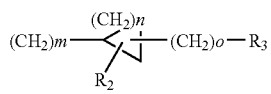

A is aryl or 5 to 6 membered heteroaryl, each of which is optionally substituted by one to five substituents selected from the group consisting of cyano, halo, $C_{1-6}$-alkyl, $C_{1-6}$-haloalkyl and $C_{1-6}$-alkoxy;
m is 1, 2 or 3;
n is 1, 2, 3, 4 or 5;
o is 0, 1 or 2;
$R_2$ is selected from the group consisting of hydrogen, hydroxyl, $C_{1-6}$-alkyl, $C_{1-6}$-haloalkyl and $C_{1-6}$-alkoxy; and
$R_3$ is selected from the group consisting of
  hydrogen, provided that $R^2 \neq$ hydrogen;
  hydroxyl;
  $C_{1-6}$-alkyl;
  $C_{1-6}$-haloalkyl;
  $C_{1-6}$-haloalkoxy;
  oxo;
  —NH(CO)—$C_{1-6}$-alkyl;
  —O—$C_{1-6}$-alkyl;
  —O—$C_{3-7}$-cycloalkyl; and
  —O-(3 to 7 membered heterocycloalkyl);
as well as pharmaceutically acceptable salts thereof.

Compounds of formula (I) may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula (I) in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Preferred compounds of formula (I) are the compounds of formula (Ia):

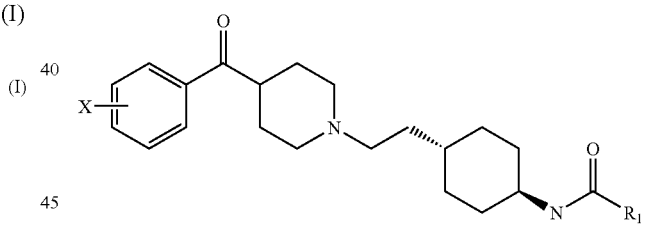

(Ia)

wherein
$R_1$:

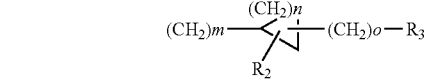

X is halo;
m is 1 or 2;
n is 2, 3 or 4;
o is 0 or 1;
$R_2$ is selected from the group consisting of hydrogen, hydroxyl, $C_{1-6}$-alkyl and $C_{1-6}$-alkoxy; and
$R_3$ is selected from the group consisting of
  hydroxyl;
  $C_{1-6}$-alkyl;
  oxo;
  —NH(CO)—$C_{1-6}$-alkyl;
  —O—$C_{1-6}$-alkyl;
  —O—$C_{3-7}$-cycloalkyl; and
  —O-(3 to 7 membered heterocycloalkyl);
as well as pharmaceutically acceptable salts thereof.

Especially preferred compounds of formula (I) are the compounds of formula (Ia):
wherein
$R_2$ is H or methyl; and
$R_3$ is hydroxyl or $C_{1-6}$-alkoxy, and $R^2$ and $—(CH_2)_o—R^3$ are bound to the same cycloalkyl carbon atom;
as well as pharmaceutically acceptable salts thereof.

Even more preferred compounds of formula (I) are the compounds of formula (Ib):

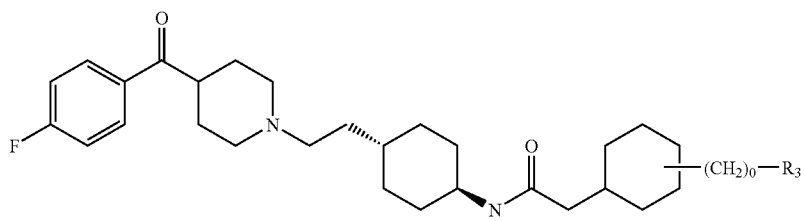

(Ib)

wherein
o is 0 or 1; and
$R_3$ is hydroxyl or $C_{1-6}$-alkoxy;
as well as pharmaceutically acceptable salts thereof.

Particularly preferred are the following compounds of formula (Ib):
wherein
o is 0;
as well as pharmaceutically acceptable salts thereof.

Also preferred compounds of formula (I) are the compounds of formula (Ic):

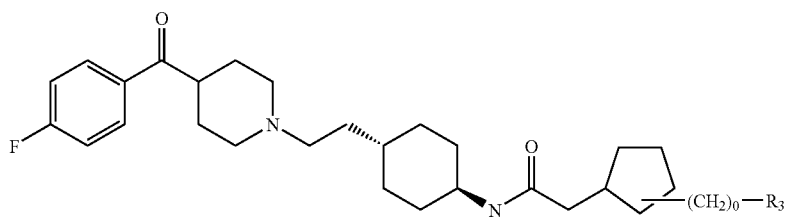

(Ic)

wherein
o is 0 or 1; and
$R_3$ is hydroxyl or $C_{1-6}$-alkoxy;
as well as pharmaceutically acceptable salts thereof.

Also preferred compounds of formula (I) are the compounds of formula (Id):

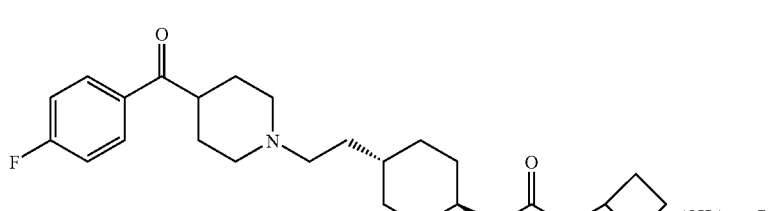

(Id)

wherein
o is 0 or 1; and
$R_3$ is hydroxyl or $C_{1-6}$-alkoxy;
as well as pharmaceutically acceptable salts thereof.

Most preferred compounds of formula (I) are the following compounds:

N-trans (4-{2-[4-(4-Fluoro-benzoyl)-piperidin-1-yl]-ethyl}-cyclohexyl)-2-cis/trans (4-hydroxy-cyclohexyl)-acetamide, N-trans (4-{2-[4-(4-Fluoro-benzoyl)-piperidin-1-yl]-ethyl}-cyclohexyl)-2-cis (4-methoxy-cyclohexyl)-acetamide, N-trans (4-{2-[4-(4-Fluoro-benzoyl)-piperidin-1-yl]-ethyl}-cyclohexyl)-2-trans (4-methoxy-cyclohexyl)-acetamide, rac-N-trans (4-{2-[4-(4-Fluoro-benzoyl)-piperidin-1-yl]-ethyl}-cyclohexyl)-2-cis (3-hydroxy-cyclohexyl)-acetamide, rac-N-trans (4-{2-[4-(4-Fluoro-benzoyl)-piperidin-1-yl]-ethyl}-cyclohexyl)-2-cis (3-methoxy-cyclohexyl)-acetamide, rac-N-trans (4-{2-[4-(4-Fluoro-benzoyl)-piperidin-1-yl]-ethyl}-cyclohexyl)-2-cis (3-hydroxy-cyclopentyl)-acetamide, rac-N-trans (4-{2-[4-(4-Fluoro-benzoyl)-piperidin-1-yl]-ethyl}-cyclohexyl)-2-trans (3-hydroxy-cyclopentyl)-acetamide, rac-N-trans (4-{2-[4-(4-Fluoro-benzoyl)-piperidin-1-yl]-ethyl}-cyclohexyl)-2-trans (3-methoxy-cyclopentyl)-acetamide, rac-N-trans (4-{2-[4-(4-Fluoro-benzoyl)-piperidin-1-yl]-ethyl}-cyclohexyl)-2-cis (3-methoxy-cyclopentyl)-acetamide, N-trans (4-{2-[4-(4-Fluoro-benzoyl)-piperidin-1-yl]-ethyl}-cyclohexyl)-2-((1S,3R)-3-methoxy-cyclopentyl)-acetamide or N-trans (4-{2-[4-(4-fluoro-benzoyl)-piperidin-1-yl]-ethyl}-cyclohexyl)-2-((1R,3S)-3-methoxy-cyclopentyl)-acetamide, N-trans (4-{2-[4-(4-Fluoro-benzoyl)-piperidin-1-yl]-ethyl}- cyclohexyl)-2-((1R,3S)-3-methoxy-cyclopentyl)-acetamide or N-trans (4-{2-[4-(4-fluoro-benzoyl)-piperidin-1-yl]-ethyl}-cyclohexyl)-2-((1S,3R)-3-methoxy-cyclopentyl)-acetamide, 2-(1,4-Dioxa-spiro[4.5]dec-8-yl)-N-trans-(4-{2-[4-(4-fluoro-benzoyl)-piperidin-1-yl]-ethyl}-cyclohexyl)-acetamide, Trans-2-(4-Ethoxy-cyclohexyl)-N-trans (4-{2-[4-(4-fluoro-benzoyl)-piperidin-1-yl]-ethyl}-cyclohexyl)-acetamide, N-trans (4-{2-[4-(4-Fluoro-benzoyl)-piperidin-1-yl]-ethyl}-cyclohexyl)-2-((1S,3S)-3-methoxy-cyclopentyl)-acetamide or N-trans (4-{2-[4-(4-fluoro-benzoyl)-piperidin-1-yl]-ethyl}-cyclohexyl)-2-((1R,3R)-3-methoxy-cyclopentyl)-acetamide, N-trans (4-{2-[4-(4-Fluoro-benzoyl)-piperidin-1-yl]-ethyl}-cyclohexyl)-2-((1R,3R)-3-methoxy-cyclopentyl)-acetamide or N-trans-(4-{2-[4-(4-fluoro-benzoyl)-piperidin-1-yl]-ethyl}-cyclohexyl)-2-((1S,3S)-3-methoxy-cyclopentyl)-acetamide, N-trans (4-{2-[4-(4-Fluoro-benzoyl)-piperidin-1-yl]-ethyl}-cyclohexyl)-2-((1R,3R)-3-methoxy-cyclohexyl)-acetamide or N-trans-(4-{2-[4-(4-fluoro-benzoyl)-piperidin-1-yl]-ethyl}-cyclohexyl)-2-((1S,3S)-3-methoxy-cyclohexyl)-acetamide, rac-N-trans (4-{2-[4-(4-Fluoro-benzoyl)-piperidin-1-yl]-ethyl}-cyclohexyl)-2-[4-(tetrahydro-furan-3-yloxy)-cyclohexyl]-acetamide, rac-2-(trans-3-Ethoxy-cyclopentyl)-N-trans-(4-{2-[4-(4-fluoro-benzoyl)-piperidin-1-yl]-ethyl}-cyclohexyl)-acetamide, N-trans (4-{2-[4-(4-Fluoro-benzoyl)-piperidin-1-yl]-ethyl}-cyclohexyl)-2-cis/trans (3-hydroxymethyl-cyclobutyl)-acetamide, N-trans (4-{2-[4-(4-Fluoro-benzoyl)-piperidin-1-yl]-ethyl}-cyclohexyl)-2-cis/trans (3-methoxymethyl-cyclobutyl)-acetamide, N-trans (4-{2-[4-(4-Fluoro-benzoyl)-piperidin-1-yl]-ethyl}-cyclohexyl)-2-trans (4-methoxymethyl-cyclohexyl)-acetamide, N-trans (4-{2-[4-(4-Fluoro-benzoyl)-piperidin-1-yl]-ethyl}-cyclohexyl)-2-(4-cis/trans-hydroxy-4-methyl-cyclohexyl)-acetamide, N-trans (4-{2-[4-(4-Fluoro-benzoyl)-piperidin-1-yl]-ethyl}-cyclohexyl)-2-(4-trans-hydroxy-4-methyl-cyclohexyl)-acetamide or N-trans (4-{2-[4-(4-fluoro-benzoyl)-piperidin-1-yl]-ethyl}-cyclohexyl)-2-(4-cis-hydroxy-4-methyl-cyclohexyl)-acetamide, N-trans (4-{2-[4-(4-Fluoro-benzoyl)-piperidin-1-yl]-ethyl}-cyclohexyl)-2-(4-cis-hydroxy-4-methyl-cyclohexyl)-acetamide or N-trans-(4-{2-[4-(4-fluoro-benzoyl)-piperidin-1-yl]-ethyl}-cyclohexyl)-2-(4-trans-hydroxy-4-methyl-cyclohexyl)-acetamide, N-trans (4-{2-[4-(4-Fluoro-benzoyl)-piperidin-1-yl]-ethyl}-cyclohexyl)-2-trans (3-methoxymethyl-cyclobutyl)-acetamide, N-trans (4-{2-[4-(4-Fluoro-benzoyl)-piperidin-1-yl]-ethyl}-cyclohexyl)-2-cis (3-methoxymethyl-cyclobutyl)-acetamide, 2-trans (4-Acetylamino-cyclohexyl)-N-trans (4-{2-[4-(4-fluoro-benzoyl)-piperidin-1-yl]-ethyl}-cyclohexyl)-acetamide, rac-N-trans-(4-{2-[4-(4-Fluoro-benzoyl)-piperidin-1-yl]-ethyl}-cyclohexyl)-2-(3-methoxymethyl-cyclopentyl)-acetamide, and rac-N-trans(4-{2-[4-(4-Fluoro-benzoyl)-piperidin-1-yl]-ethyl}-cyclohexyl)-3-(4-methoxy-cyclohexyl)-propionamide.

The preparation of compounds of formula (I) of the present invention can be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the description or in the examples, or by methods known in the art.

In the following schemes, A and $R_1$ are as described hereinabove.

Scheme 1

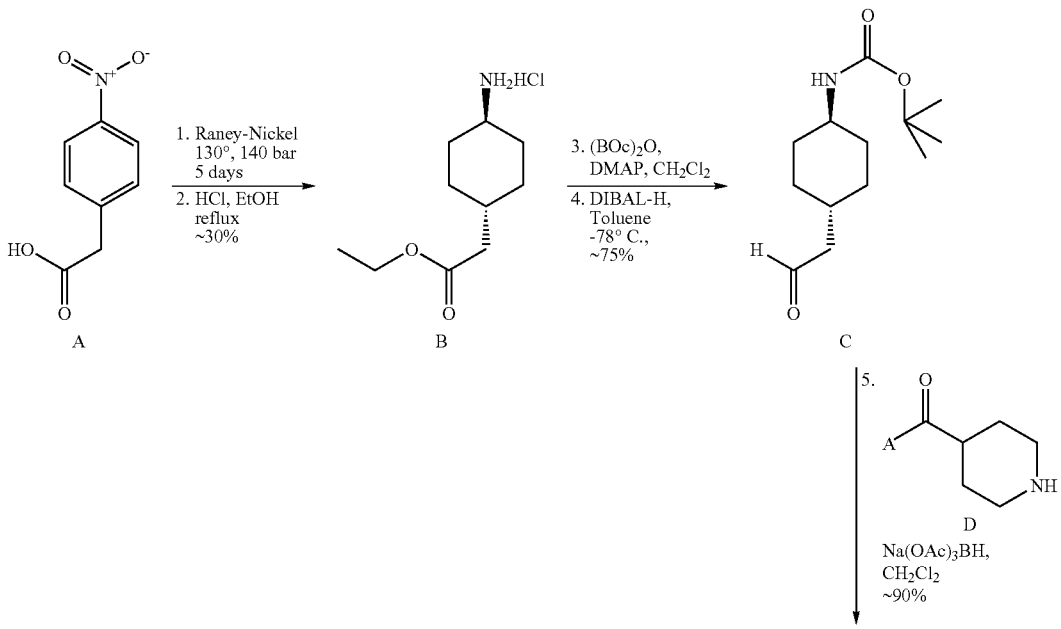

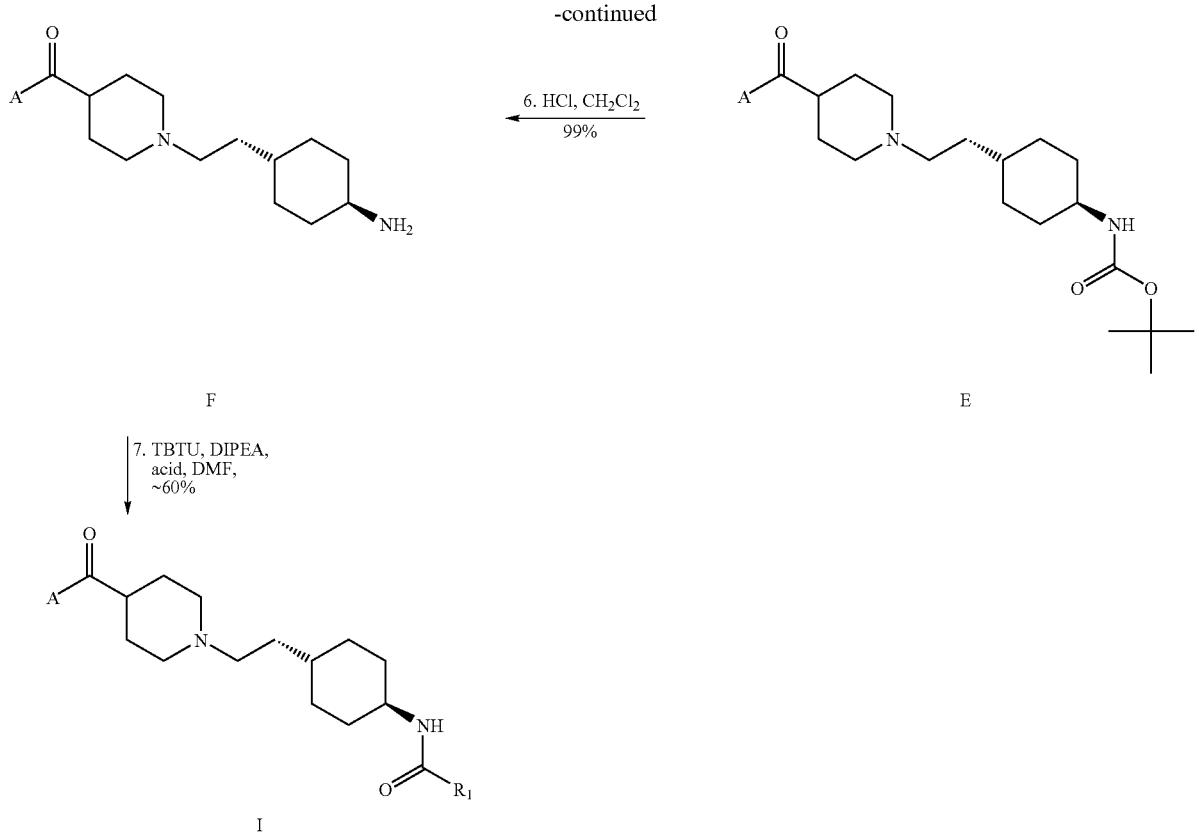

Heteroaryl or benzoyl-piperidin-1-yl trans-ethyl-cyclohexyl-amides or trans-1,4-cyclohexyl ethyl derivates of formula (I) can be prepared as depicted in scheme 1 starting from 4-nitro-phenylacetic acid that was hydrogenated using raney nickel as catalyst. The hydrogenation with nickel leads preferentially to the desired trans-isomer (according to Journal of Medicinal Chemistry, 1998, 41, 760-771). Preparing the ethyl ester according to methods known to those skilled in the art and described in the mentioned literature (e.g by treatment with ethanol on the presence of an acid such as HCl) and crystallizing the HCl salt resolves the cis/trans mixture and results in the isolation of the pure trans amino ester chloride B. Reaction with a protecting group such as tert-butyl dicarbonate on the presence of a base like triethylamine and a catalyst like dimethylaminopyridine and reduction with diisobutylaluminium hydride (DIBAL-H) in an appropriate solvent such as, e.g. toluene at −78° C. gives the aldehyde C which can be used without purification on the next step. Reductive amination of aldehyde C with a substituted phenyl or heteroaryl piperidin-4-yl-methanone D either commercially available or accessible by methods described in references by methods described in this patent or by methods known in the art in the presence of a solvent like dichloromethane or 1,2-dichlorethane and a reducing agent such as sodium triacetoxy borohydride yields intermediate E. Removal of the Boc protective group under acidic conditions such as trifluoroacetic acid or hydrochloric acid in a suitable solvent such as, e.g. THF, EtOAc or dichlormethane yields the trans-amino cyclohexyl ethyl intermediate F (usually the TFA or hydrochloride salt). The coupling of the amine intermediate F with carboxylic acids is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents such as, e.g. N,N'-carbonyldiimidazole (CDI) or O-benzotriazol-1-yl-N,N,N',N'-tetramethyluronium tetrafluoroborate (TBTU) in a suitable solvent like, e.g. dimethylformamide (DMF) or dioxane in the presence of a base (e.g. triethylamine or diisopropylethylamine) to yield compounds of formula (I). The carboxylic acids used on the coupling (or their salts) are commercially available, easily accessible by methods well known in the art or by methods described on this patent.

The ability of the compounds to bind to the 5-HT$_{2A}$, D$_3$ and D$_2$ receptors was determined using radioligand binding to cloned receptors selectively expressed in HEK-293 EBNA cells.

Membrane Preparation for Human D$_2$, Human D$_3$ and Human 5-HT$_{2A}$ Receptors HEK-293 EBNA cells were transiently transfected with expression plasmids encoding for the human D$_2$ or D$_3$ dopamine- or for the human 5-HT$_{2A}$ serotonin receptor, respectively. The cells were harvested 48 h post-transfection, washed three times with cold PBS and stored at −80° C. prior to use. The pellet was suspended in cold 50 mM Tris-HCl buffer containing 10 mM EDTA (pH 7.4) and homogenized with a Polytron (Kinematica AG, Basel, Switzerland) for 20-30 sec at 12.000 rpm. After centrifugation at 48.000×g for 30 min at 4° C., the pellet was resuspended in cold 10 mM Tris-HCl buffer containing 0.1 mM EDTA (pH 7.4), homogenized, and centrifuged as above. This pellet was further resuspended in a smaller volume of ice cold 10 mM Tris-HCl buffer containing 0.1 mM EDTA (pH 7.4) and homogenized with a Polytron for 20-30 sec at 12.000 rpm. The protein content of this homogenate was determined with the Bio-Rad (Bradford) Protein Assay (Biorad Laboratories GmbH, München, Germany) according to the instructions of the manufacturer using gamma globulin as the standard. This homogenate was stored at −80° C. in aliquots and thawed immediately prior to use.

Radioligand Binding Assay Conditions

Aliquots of membrane preparations were thawed at RT, resuspended in assay buffer ($D_2$, $D_3$: 50 mM Tris-HCl, 120 mM NaCl, 5 mM $MgCl_2$, 1 mM EDTA, 5 mM KCl, 1.5 mM $CaCl_2$, pH=7.4; $5\text{-}HT_{2A}$: 50 mM Tris-HCl, 10 mM $MgCl_2$, 1 mM EGTA, pH=7.4), homogenized with a Polytron for 20-30 sec at 12.000 rpm and adjusted to a final concentration of approximately 7.5 μg protein/well ($D_2$, $D_3$) and 15 μg protein/well ($5\text{-}HT_{2A}$), respectively.

The binding affinity (Ki) of the compounds was determined using radioligand binding. Membranes were incubated in a total volume of 200 μl with a fixed concentration of radioligand (final concentration approximately 0.7 nM [$^3$H]-spiperone for $D_2$, 0.5 nM [$^3$H]-spiperone for $D_3$, and 1.1 nM [$^3$H]-ketanserin for $5\text{-}HT_{2A}$) and ten concentrations of test compound in ranging between 10 μM-0.1 nM for 1 h at RT. At the end of the incubation, the reaction mixtures were filtered on to unifilter 96-well white microplates with bonded GF/C filters (Packard BioScience, Zürich, Switzerland; preincubated for 1 h in 0.1% polyethylenimine (PEI) in assay buffer) with a Filtermate 196 harvester (Packard BioScience) and washed 3 times with cold assay buffer. The nonspecific binding was determined with equally composed reaction mixtures in the presence of 10 μM unlabeled spiperone. Per well 45 μl of Microscint 40 (Perkin Elmer, Schwerzenbach, Switzerland) was added, plates for sealed, shaken for 20 min and counted for 3 min on a Topcount Microplate Scintillation Counter (Canberra Packard SA, Zürich, Switzerland) with quenching correction.

Data Calculation

The CPM value for each duplicate of a concentration of competing compound was averaged (y1), then the % specific binding was calculated according to the equation (((y1-nonspecific)/(total binding-non-specific))×100). Graphs were plotted with the % specific binding using XLfit, a curve fitting program that iteratively plots the data using Levenburg Marquardt algorithm. The single site competition analysis equation used was $y=A+((B-A)/(1+((x/C)^D)))$, where y is the % specific binding, A is the minimum y, B is the maximum y, C is the $IC_{50}$, x is the $\log_{10}$ of the concentration of the competing compound and D is the slope of the curve (the Hill Coefficient). From these curves the $IC_{50}$ (inhibition concentration at which 50% specific binding of the radioligand was displaced) and Hill coefficient were determined. The affinity constant (Ki) was calculated using the Cheng-Prusoff equation $Ki=(IC_{50}/1+([L]/Kd)$, where [L] is the concentration of radioligand and Kd is the dissociation constant of the radioligand at the receptor as determined by the saturation isotherm.

The compounds of the present invention are selective dual modulators of the serotonin $5\text{-}HT_{2a}$ and dopamine $D_3$ receptors as this is shown with the activity table hereinafter which gives the Ki values in nM for the serotonin $5\text{-}HT_{2a}$, dopamine $D_3$ and dopamine $D_2$ receptors for some examples of the compounds of the present invention:

Activity table

| Ex. | Systematic Name | Ki ($D_3$) | Ki ($5HT_{2a}$) | Ki ($D_2$) |
|---|---|---|---|---|
| 1 | N-trans (4-{2-[4-(4-Fluoro-benzoyl)-piperidin-1-yl]-ethyl}-cyclohexyl)-2-cis/trans (4-hydroxy-cyclohexyl)-acetamide | 43 | 13 | 1491 |
| 2 | N-trans (4-{2-[4-(4-Fluoro-benzoyl)-piperidin-1-yl]-ethyl}-cyclohexyl)-2-cis (4-methoxy-cyclohexyl)-acetamide | 28 | 6 | 1505 |
| 3 | N-trans (4-{2-[4-(4-Fluoro-benzoyl)-piperidin-1-yl]-ethyl}-cyclohexyl)-2-trans (4-methoxy-cyclohexyl)-acetamide | 24 | 6 | 1278 |
| 4 | rac-N-trans (4-{2-[4-(4-Fluoro-benzoyl)-piperidin-1-yl]-ethyl}-cyclohexyl)-2-cis (3-hydroxy-cyclohexyl)-acetamide | 43 | 14 | 1014 |
| 5 | rac-N-trans (4-{2-[4-(4-Fluoro-benzoyl)-piperidin-1-yl]-ethyl}-cyclohexyl)-2-cis (3-methoxy-cyclohexyl)-acetamide | 45 | 19 | 1186 |
| 6 | rac-trans N-(4-{2-[4-(4-Fluoro-benzoyl)-piperidin-1-yl]-ethyl}-cyclohexyl)-2-cis (3-hydroxy-cyclopentyl)-acetamide | 35 | 11 | 828 |
| 7 | rac-N-trans (4-{2-[4-(4-Fluoro-benzoyl)-piperidin-1-yl]-ethyl}-cyclohexyl)-2-trans (3-hydroxy-cyclopentyl)-acetamide | 19 | 16 | 807 |
| 8 | rac-N-trans (4-{2-[4-(4-Fluoro-benzoyl)-piperidin-1-yl]-ethyl}-cyclohexyl)-2-trans (3-methoxy-cyclopentyl)-acetamide | 23 | 16 | 1173 |
| 9 | rac-N-trans (4-{2-[4-(4-Fluoro-benzoyl)-piperidin-1-yl]-ethyl}-cyclohexyl)-2-cis (3-methoxy-cyclopentyl)-acetamide | 42 | 6 | 890 |
| 10 | N-trans (4-{2-[4-(4-Fluoro-benzoyl)-piperidin-1-yl]-ethyl}-cyclohexyl)-2-((1S,3R)-3-methoxy-cyclopentyl)-acetamide or N-trans-(4-{2-[4-(4-fluoro-benzoyl)-piperidin-1-yl]-ethyl}-cyclohexyl)-2-((1R,3S)-3-methoxy-cyclopentyl)-acetamide | 56 | 5 | 1252 |
| 11 | N-trans (4-{2-[4-(4-Fluoro-benzoyl)-piperidin-1-yl]-ethyl}-cyclohexyl)-2-((1R,3S)-3-methoxy-cyclopentyl)-acetamide or N-trans-(4-{2-[4-(4-fluoro-benzoyl)-piperidin-1-yl]-ethyl}-cyclohexyl)-2-((1S,3R)-3-methoxy-cyclopentyl)-acetamide | 62 | 11 | 1818 |
| 12 | 2-(1,4-Dioxa-spiro[4.5]dec-8-yl)-N-trans (4-{2-[4-(4-fluoro-benzoyl)-piperidin-1-yl]-ethyl}-cyclohexyl)-acetamide | 24 | 6 | 1739 |
| 13 | Trans-2-(4-Ethoxy-cyclohexyl)-N-trans (4-{2-[4-(4-fluoro-benzoyl)-piperidin-1-yl]-ethyl}-cyclohexyl)-acetamide | 33 | 13 | 1398 |
| 14 | N-trans (4-{2-[4-(4-Fluoro-benzoyl)-piperidin-1-yl]-ethyl}-cyclohexyl)-2-((1S,3S)-3-methoxy-cyclopentyl)-acetamide or N-trans (4-{2-[4-(4-fluoro-benzoyl)-piperidin-1-yl]-ethyl}-cyclohexyl)-2-((1R,3R)-3-methoxy-cyclopentyl)-acetamide | 18 | 7 | 546 |
| 15 | N-trans (4-{2-[4-(4-Fluoro-benzoyl)-piperidin-1-yl]-ethyl}-cyclohexyl)-2-((1R,3R)-3-methoxy-cyclopentyl)-acetamide or N-trans (4-{2-[4-(4-fluoro-benzoyl)-piperidin-1-yl]-ethyl}-cyclohexyl)-2-((1S,3S)-3-methoxy-cyclopentyl)-acetamide | 34 | 16 | 1751 |
| 16 | N-trans (4-{2-[4-(4-Fluoro-benzoyl)-piperidin-1-yl]-ethyl}-cyclohexyl)-2-((1R,3R)-3-methoxy-cyclohexyl)-acetamide or N-trans-(4-{2-[4-(4-fluoro-benzoyl)-piperidin-1-yl]-ethyl}-cyclohexyl)-2-((1S,3S)-3-methoxy-cyclohexyl)-acetamide | 35 | 7 | 1249 |

-continued

Activity table

| Ex. | Systematic Name | Ki (D$_3$) | Ki (5HT$_{2a}$) | Ki (D$_2$) |
|---|---|---|---|---|
| 17 | rac-N-trans (4-{2-[4-(4-Fluoro-benzoyl)-piperidin-1-yl]-ethyl}-cyclohexyl)-2-[4-(tetrahydro-furan-3-yloxy)-cyclohexyl]-acetamide | 40 | 11 | 2605 |
| 18 | rac-2-(trans-3-Ethoxy-cyclopentyl)-N-trans-(4-{2-[4-(4-fluoro-benzoyl)-piperidin-1-yl]-ethyl}-cyclohexyl)-acetamide | 42 | 28 | 1943 |
| 19 | N-trans (4-{2-[4-(4-Fluoro-benzoyl)-piperidin-1-yl]-ethyl}-cyclohexyl)-2-cis/trans (3-hydroxymethyl-cyclobutyl)-acetamide | 28 | 11 | 1003 |
| 20 | N-trans (4-{2-[4-(4-Fluoro-benzoyl)-piperidin-1-yl]-ethyl}-cyclohexyl)-2-cis/trans (3-methoxymethyl-cyclobutyl)-acetamide | 27 | 12 | 1360 |
| 21 | N-trans (4-{2-[4-(4-Fluoro-benzoyl)-piperidin-1-yl]-ethyl}-cyclohexyl)-2-trans (4-methoxymethyl-cyclohexyl)-acetamide | 25 | 5 | 1010 |
| 22 | N-trans (4-{2-[4-(4-Fluoro-benzoyl)-piperidin-1-yl]-ethyl}-cyclohexyl)-2-(4-cis/trans-hydroxy-4-methyl-cyclohexyl)-acetamide | 56 | 12 | 1364 |
| 23 | N-trans (4-{2-[4-(4-Fluoro-benzoyl)-piperidin-1-yl]-ethyl}-cyclohexyl)-2-(4-trans-hydroxy-4-methyl-cyclohexyl)-acetamide or N-trans-(4-{2-[4-(4-fluoro-benzoyl)-piperidin-1-yl]-ethyl}-cyclohexyl)-2-(4-cis-hydroxy-4-methyl-cyclohexyl)-acetamide | 49 | 7 | 1303 |
| 24 | N-trans (4-{2-[4-(4-Fluoro-benzoyl)-piperidin-1-yl]-ethyl}-cyclohexyl)-2-(4-cis-hydroxy-4-methyl-cyclohexyl)-acetamide or N-trans-(4-{2-[4-(4-fluoro-benzoyl)-piperidin-1-yl]-ethyl}-cyclohexyl)-2-(4-trans-hydroxy-4-methyl-cyclohexyl)-acetamide | 43 | 9 | 1198 |
| 25 | N-trans (4-{2-[4-(4-Fluoro-benzoyl)-piperidin-1-yl]-ethyl}-cyclohexyl)-2-trans (3-methoxymethyl-cyclobutyl)-acetamide | 27 | 9 | 1862 |
| 26 | N-trans (4-{2-[4-(4-Fluoro-benzoyl)-piperidin-1-yl]-ethyl}-cyclohexyl)-2-cis (3-methoxymethyl-cyclobutyl)-acetamide | 26 | 6 | 2035 |
| 27 | 2-trans (4-Acetylamino-cyclohexyl)-N-trans-(4-{2-[4-(4-fluoro-benzoyl)-piperidin-1-yl]-ethyl}-cyclohexyl)-acetamide | 44 | 34 | 2066 |
| 28 | rac-N-trans (4-{2-[4-(4-Fluoro-benzoyl)-piperidin-1-yl]-ethyl}-cyclohexyl)-2-(3-methoxymethyl-cyclopentyl)-acetamide | 33 | 7 | 1295 |
| 29 | rac-N-trans (4-{2-[4-(4-Fluoro-benzoyl)-piperidin-1-yl]-ethyl}-cyclohexyl)-3-(4-methoxy-cyclohexyl)-propionamide | 41 | 7 | 1415 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such as carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injectable solutions.

As mentioned hereinabove, the compounds of the invention have high affinity for the dopamine D$_3$ and serotonin 5-HT$_{2A}$ receptors and are expected to be effective in the treatment of psychotic disorders which include schizophrenia, schizoaffective disorders, bipolar disease, mania, psychotic depression, and other psychoses involving paranoia and delusions (Reavill-C, et al. (2000) Pharmacological actions of a novel, high-affinity, and selective human dopamine D3 receptor antagonist, SB-277011-A. JPET 294:1154-1165; Harrison, P. J. (1999) Neurochemical alterations in schizophrenia affecting the putative receptor targets of atypical antipsychotics. Focus on dopamine (D1, D3, D4) and 5-HT2A receptors. Br. J. Psychiatry Suppl. 38, 12-22; de Angelis, L. (2002) 5-HT2A antagonists in psychiatric disorders. Curr. Opin. Investig. Drugs 3, 106-112; Joyce, J. N. and Millan, M. J., (2005) Dopamine D3 receptor antagonists as therapeutic agents. Drug Discovery Today, 1 July, Vol. 10, No. 13, P. 917-25); drug dependency and abuse and withdrawal (Vorel, S. R. et al. (2002) Dopamine D3 receptor antagonism inhibits cocaine-seeking and cocaine-enhanced brain reward in rats. J. Neurosci., 22, 9595-9603; Campos, A. C. et al. (2003) The dopamine D3 receptor antagonist SB277011A antagonizes nicotine-enhanced brain-stimulation reward in rat. Soc. Neurosci. Abstr., 322.8; Ashby, et al. (2003) Acute administration of the selective D3 receptor antagonist SB-277011-A blocks the acquisition and expression of the conditioned place preference response to heroin in male rats. Synapse, 48, 154-156); anxiety, and depression (Reavill-C et al. (2000) Pharmacological actions of a novel, high-affinity, and selective human dopamine D3 receptor antagonist, SB-277011-A. JPET 294: 1154-1165; Drescher, K. et al. (2002) In vivo effects of the selective dopamine D3 receptor antagonist A-437203. Am. Soc. Neurosci. 894.6).

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention:

Synthesis of Intermediates

Intermediate F

Trans {1-[2-(4-amino-cyclohexyl)-ethyl]-piperidin-4-yl}-(4-fluoro-phenyl)-methanone hydrochloride

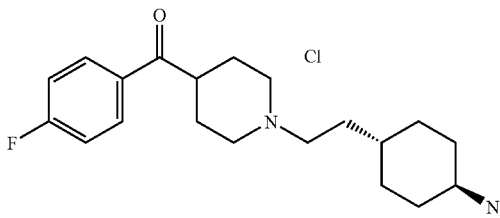

Step 1: Trans (4-Amino-cyclohexyl)-acetic acid ethyl ester (4-Nitro-phenyl)-acetic acid (50 g, 276 mmol) was added to a stirred solution of 22.08 g of 50% sodium hydroxide solution in 450 ml deionizated water. The clear yellow solution is transferred into a high-pressure autoclave that it charged with 30 g (511 mmol) of water-wet sponge nickel catalyst. The autoclave is sealed, flushed with nitrogen and then pressurized to 115 bar with hydrogen. The reaction mixture is stirred and heated to 125° C. for 48 h. At that time the autoclave is cooled, vented and charged under nitrogen with another 30 g (511 mmol) of the sponge nickel catalyst. The autoclave is flushed again with nitrogen and then pressurized to 115 bar and the vessel is heated to 130° C. while stirring (a maximum pressure of 130 bars is observed). Hydrogenation is continued for 5 days to 130° C. The autoclave is then cooled, vented and flushed with nitrogen and the contents are removed and filtered through filter aid to remove catalyst. After removal of the solvent, 74 g of crude material was obtained. The intermediated is used directly in the next step without purification. MS (m/e): 158.3 (M+H$^+$)

Step 2: Trans (4-Amino-cyclohexyl)-acetic acid ethyl ester hydrochloride

A solution of the Trans-(4-amino-cyclohexyl)-acetic acid obtained (74 g, 476 mmol) was adjusted to pH 5 with 25% HCl. The mixture was evaporated to dryness and dried under vacuum overnight. The residue was suspended in 146 mL of a 6.5N ethanolic HCl solution and 0.6 L of ethanol was added to the mixture. After 4 h refluxing, the mixture was cooled and filtered and the filtrate was concentrated to dryness under vacuum. The residue was dissolved in ethanol, treated with ether and cooled overnight in the refrigerator, to give the trans-(4-amino-cyclohexyl)-acetic acid ethyl ester hydrochloride (19.7 g, 32% on the two steps) as a white solid which was filtered and dried under vacuum. MS (m/e): 186.1 (M+H$^+$)

Step 3: Trans (4-tert-Butoxycarbonylamino-cyclohexyl)-acetic acid ethyl ester

To a solution of trans-(4-Amino-cyclohexyl)-acetic acid ethyl ester (1.28 g, 7 mmol), in dichloromethane (15 mL), di-tert-butyl-dicarbonate (2.26 g, 10 mmol), triethylamine (0.699 mL, 7 mmol) and 4-dimethylaminopyridine (0.042 mL, 0.35 mmol) were added. The mixture was stirred for 8 h until TLC indicated completion of the reaction. Water was added and the solution was extracted three times with dichloromethane. The combined organic layers were washed with water and brine, dried over magnesium sulfate, filtered and evaporated. The crude product was purified by flash-chromatography on silica gel with hexane:ethyl acetate (4:2 to 3:2) to give 1.2 g (60%) of the product as a white solid. MS (m/e): 284.4 (M–H$^+$).

Step 4: Trans-[4-(2-Oxo-ethyl)-cyclohexyl]-carbamic acid tert-butyl ester

To a solution of trans-(4-tert-Butoxycarbonylamino-cyclohexyl)-acetic acid ethyl ester (1.04 g, 4 mmol), in toluene (10 mL) at −78° C. a 1.2M solution of DIBAL-H (5.1 mL, 6 mmol) in toluene was added. The mixture was stirred at −78° C. until TLC after 0.5 h indicated completion of the reaction. Water was added and the solution was extracted three times with dichloromethane. The combined organic layers were washed with water and brine, dried over magnesium sulfate, filtered and evaporated. The crude product was used without purification on the next step. MS (m/e): 242.3 (M+H$^+$).

Step 5: Trans-(4-{2-[4-(4-Fluoro-benzoyl)-piperidin-1-yl]-ethyl}-cyclohexyl)-carbamic acid tert-butyl ester A mixture of 4-(4-fluorobenzoyl)piperidine hydrochloride (0.850 g, 3.4 mmol), trans-[4-(2-Oxo-ethyl)-cyclohexyl]-carbamic acid tert-butyl ester (0.926 g, 4 mmol), in dichloromethane (10 mL) was stirred for 2 hours at room temperature and sodium triacetoxyborohydride (1.33 g, 6 mmol) was added and the resulting solution was stirred for 12 hours until the TLC indicated completion of the reaction. The mixture was filtrated and concentrated to dryness and purified with column chromatography on silica gel using CH$_2$Cl$_2$—CH$_2$Cl$_2$/MeOH (1-9:1). The product fractions were concentrated to give 1.4 g (3.25 mmol, 93.2% yield) of a light yellow solid. MS (m/e): 433.4 (M+H$^+$).

Step 6: Trans-{1-[2-(4-Amino-cyclohexyl)-ethyl]-piperidin-4-yl}-(4-fluoro-phenyl)-methanone hydrochloride Trans-(4-{2-[4-(4-fluoro-benzoyl)-piperidin-1-yl]-ethyl}-cyclohexyl)-carbamic acid tert-butyl ester (1.4 g, 3.24 mmol) was dissolved in 2 ml dichloromethane and 4N HCl in dioxane (9.7 ml, 38.8 mmol) was added. The white suspension was stirred for 4 hours at room temperature, diluted with diisopropylether and filtered. The crystals were washed with diisopropylether and dried for 2 hours at 50° C. and <20 mbar, to get the desired salt as a white solid (1.2 g, 100%) [MS: m/e=333.3 (M+H$^+$)].

Example 1

N-trans (4-{2-[4-(4-Fluoro-benzoyl)-piperidin-1-yl]-ethyl}-cyclohexyl)-2-cis/trans (4-hydroxy-cyclohexyl)-acetamide

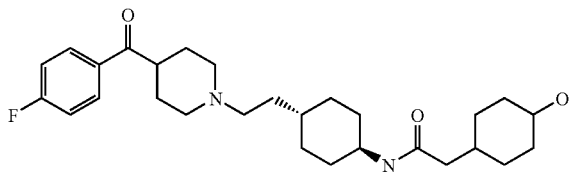

Step 1: (4-Hydroxy-cyclohexyl)-acetic acid methyl ester

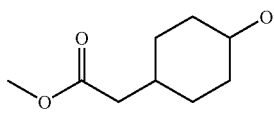

The title compound can be prepared in accordance with literature *Journal of the American Chemical Society* (1948), 70 1898-9 and esterification of the resulting acid.

Step 2: N-trans (4-{2-[4-(4-Fluoro-benzoyl)-piperidin-1-yl]-ethyl}-cyclohexyl)-2-cis/trans (4-hydroxy-cyclohexyl)-acetamide (4-Hydroxy-cyclohexyl)-acetic acid methyl ester (91 mg, 0.53 mmol) was dissolved in 2 ml dichloromethane. Potassium trimethylsilanolate KO'SiMe3 (90 mg, 0.70 mmol) was added and the suspension stirred for 16 hours at room temperature. The solvent was evaporated and trans-{1-[2-(4-amino-cyclohexyl)-ethyl]-piperidin-4-yl}-(4-fluoro-phenyl)-methanone hydrochloride (130 mg, 0.35 mmol) (intermediate F) in 1 ml DMF was added. N,N-Diisopropylethylamine (180 μl, 1.06 mmol) and 2-(1H-benzotriazol-1-yl)-1,1,3,3-tetramethyl uronium tetrafluoroborate TBTU (136 mg, 0.42 mmol) were added and the reaction stirred for 2 hours at room temperature. The reaction mixture was quenched with saturated NaHCO3-solution and extracted with dichloromethane. The organic extract was washed with brine, dried with sodium sulfate, filtered and evaporated. The crude product was purified by flash chromatography on silica gel (dichloromethane/methanol 100:0→90:10 gradient). The desired compound was obtained as a white solid (88 mg, 53%), MS: m/e=473.3/474.3 (M+H$^+$).

Example 2

N-trans (4-{2-[4-(4-Fluoro-benzoyl)-piperidin-1-yl]-ethyl}-cyclohexyl)-2-cis (4-methoxy-cyclohexyl)-acetamide

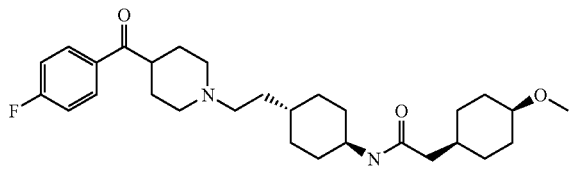

Step 1: Cis (4-Hydroxy-cyclohexyl)-acetic acid

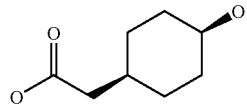

The title compound can be prepared in accordance with literature *Journal of the American Chemical Society* (1948), 70 1898-9.

Step 2: Cis (4-Hydroxy-cyclohexyl)-acetic acid methyl ester

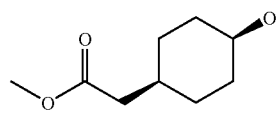

The ester can be prepared by refluxing the corresponding acid in methanol and catalytic sulfuric acid for 4 hours.

Step 3: Cis (4-Methoxy-cyclohexyl)-acetic acid methyl ester

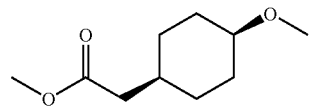

Cis (4-Hydroxy-cyclohexyl)-acetic acid methyl ester (500 mg, 2.90 mmol) were dissolved in 1.5 ml DMF and cooled to 0-5° C. Sodium hydride (190 mg, 4.35 mmol, 55%) and iodomethane (3.62 ml, 23.2 mmol) were added and the reaction mixture stirred for 4 hours at 0-5° C. The reaction mixture was quenched with saturated NaHCO3-solution and extracted with dichloromethane. The organic extract was washed with brine, dried with sodium sulfate, filtered and evaporated. The crude product (561 mg, quant.) was obtained as a colourless oil and used without any further purification for the next step.

Step 4: N-trans (4-{2-[4-(4-Fluoro-benzoyl)-piperidin-1-yl]-ethyl}-cyclohexyl)-2-cis (4-methoxy-cyclohexyl)-acetamide The title compound, MS: m/e=487.4/488.3 (M+H$^+$), was prepared in accordance with the general method of example 1, step 2 from trans-{1-[2-(4-amino-cyclohexyl)-ethyl]-piperidin-4-yl}-(4-fluoro-phenyl)-methanone hydrochloride (intermediate F) and cis (4-methoxy-cyclohexyl)-acetic acid methyl ester.

Example 3

N-trans (4-{2-[4-(4-Fluoro-benzoyl)-piperidin-1-yl]-ethyl}-cyclohexyl)-2-trans (4-methoxy-cyclohexyl)-acetamide

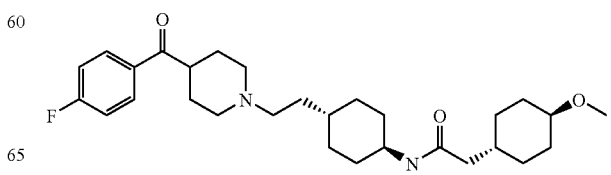

Step 1: trans (4-Methoxy-cyclohexyl)-acetic acid methyl ester

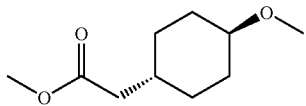

The title compound was prepared in accordance with example 2, (step 1, step 2 and step 3).

Step 2: N-trans (4-{2-[4-(4-Fluoro-benzoyl)-piperidin-1-yl]-ethyl}-cyclohexyl)-2-trans (4-methoxy-cyclohexyl)-acetamide The title compound, MS: m/e=487.4/488.3 (M+H$^+$), was prepared by acid salt formation and amide coupling as described on example 1, step 2 from Trans-{1-[2-(4-amino-cyclohexyl)-ethyl]-piperidin-4-yl}-(4-fluoro-phenyl)-methanone hydrochloride (intermediate F) and Trans-(4-methoxy-cyclohexyl)-acetic acid methyl ester.

Example 4 rac-N-trans (4-{2-[4-(4-Fluoro-benzoyl)-piperidin-1-yl]-ethyl}-cyclohexyl)-2-cis (3-hydroxy-cyclohexyl)-acetamide

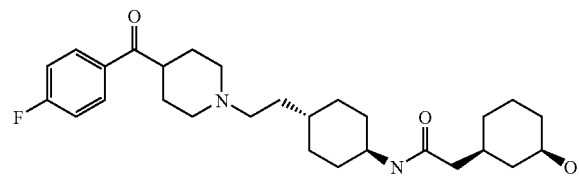

Step 1: rac-cis (3-Hydroxy-cyclohexyl)-acetic acid

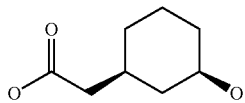

The title compound, MS: m/e=157.0 (M−H$^+$), can be prepared in accordance with literature *Tetrahedron*, 38(24), 3641-7; 1982 from 3-hydroxyphenylacetic acid.

Step 2: rac-N-trans-(4-{2-[4-(4-Fluoro-benzoyl)-piperidin-1-yl]-ethyl}-cyclohexyl)-2-cis (3-hydroxy-cyclohexyl)-acetamide Trans-{1-[2-(4-amino-cyclohexyl)-ethyl]-piperidin-4-yl}-(4-fluoro-phenyl)-methanone hydrochloride (intermediate F) (150 mg, 0.41 mmol), rac-cis-(3-hydroxy-cyclohexyl)-acetic acid (103 mg, 0.65 mmol), N,N-diisopropylethylamine (210 µl, 1.22 mmol) and 2-(1H-benzotriazol-1-yl)-1,1,3,3-tetramethyl uronium tetrafluoroborate [TBTU] (157 mg, 0.0.49 mmol) were dissolved in 1 ml DMF and stirred for 2 hours at room temperature. The reaction mixture was quenched with saturated NaHCO3-solution and extracted with dichloromethane. The organic extract was washed with brine, dried with sodium sulfate, filtered and evaporated. The crude product was purified by flash chromatography on silica gel (dichloromethane/methanol 100:0→90:10 gradient). The desired compound was obtained as a white solid (123 mg, 64%), MS: m/e=473.2/474.1 (M+H$^+$).

Example 5 rac-N-trans (4-{2-[4-(4-Fluoro-benzoyl)-piperidin-1-yl]-ethyl}-cyclohexyl)-2-cis (3-methoxy-cyclohexyl)-acetamide

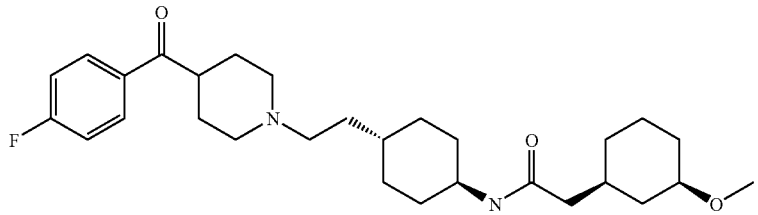

Step 1: rac-cis (3-Hydroxy-cyclohexyl)-acetic acid methyl ester

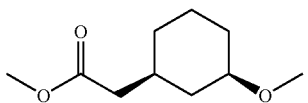

The title compound was prepared in accordance with the general method of example 2, step 2 from rac-cis-(3-hydroxy-cyclohexyl)-acetic acid (example 4, step 1).

Step 2: rac-cis (3-Methoxy-cyclohexyl)-acetic acid methyl ester

The title compound was prepared in accordance with the general method of example 2, step 3.

Step 3: rac-N-trans (4-{2-[4-(4-Fluoro-benzoyl)-piperidin-1-yl]-ethyl}-cyclohexyl)-2-cis (3-methoxy-cyclohexyl)-acetamide The title compound, MS: m/e=487.4/488.2 (M+H$^+$), was prepared in accordance with the general method of example 1, step 2 from trans-{1-[2-(4-amino-cyclohexyl)-ethyl]-piperidin-4-yl}-(4-fluoro-phenyl)-methanone hydrochloride (Example A) and rac-cis (3-methoxy-cyclohexyl)-acetic acid methyl ester.

Example 6 rac-trans-N (4-{2-[4-(4-Fluoro-benzoyl)-piperidin-1-yl]-ethyl}-cyclohexyl)-2-cis (3-hydroxy-cyclopentyl)-acetamide

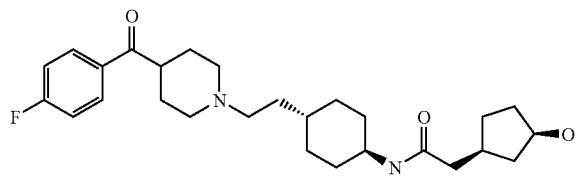

Step 1: rac-cis (3-Hydroxy-cyclopentyl)-acetic acid

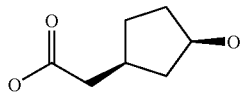

The title compound can be prepared in accordance with literature *Helvetica Chimica Acta—Vol.* 75 (1992) Page 1945 and 1950.

Step 2: rac-trans-N-(4-{2-[4-(4-Fluoro-benzoyl)-piperidin-1-yl]-ethyl}-cyclohexyl)-2-cis (3-hydroxy-cyclopentyl)-acetamide The title compound, MS: m/e=459.5/460.4 (M+H⁺), was prepared in accordance with the general method of example 4, step 2 from trans-{1-[2-(4-amino-cyclohexyl)-ethyl]-piperidin-4-yl}-(4-fluoro-phenyl)-methanone hydrochloride (Example A) and rac-cis-(3-hydroxy-cyclopentyl)-acetic acid.

Example 7 rac-N-trans (4-{2-[4-(4-Fluoro-benzoyl)-piperidin-1-yl]-ethyl}-cyclohexyl)-2-trans (3-hydroxy-cyclopentyl)-acetamide

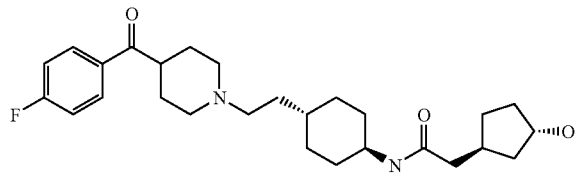

Step 1: rac-trans (3-Hydroxy-cyclopentyl)-acetic acid methyl ester

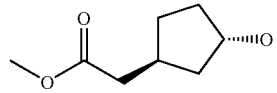

The title compound can be prepared in accordance with literature *Helvetica Chimica Acta—Vol.* 75 (1992) Page 1945 and 1950.

Step 2: rac-N-trans (4-{2-[4-(4-Fluoro-benzoyl)-piperidin-1-yl]-ethyl}-cyclohexyl)-2-trans (3-hydroxy-cyclopentyl)-acetamide rac-Trans-(3-Hydroxy-cyclopentyl)-acetic acid methyl ester (77 mg, 0.49 mmol) was dissolved in 2 ml THF, 1 ml methanol and 1 ml water. Lithium hydroxide monohydrate (51 mg, 1.22 mmol) was added and the reaction mixture stirred for 16 hours at room temperature. The organic solvent was evaporated and the aqueous mixture was acidified with 2N HCl to pH 1. The mixture was evaporated to dryness and trans-{1-[2-(4-amino-cyclohexyl)-ethyl]-piperidin-4-yl}-(4-fluoro-phenyl)-methanone hydrochloride (150 mg, 0.41 mmol) (Example A) in 1 ml DMF was added. N,N-Diisopropylethylamine (350 μl, 2.03 mmol) and 2-(1H-benzotriazol-1-yl)-1,1,3,3-tetramethyl uronium tetrafluoroborate [TBTU] (157 mg, 0.49 mmol) were added and the reaction stirred for 2 hours at room temperature. The reaction mixture was quenched with saturated NaHCO3-solution and extracted with dichloromethane. The organic extract was washed with brine, dried with sodium sulfate, filtered and evaporated. The crude product was purified by flash chromatography on silica gel (dichloromethane/methanol 100:0→90:10 gradient). The desired compound was obtained as a white solid (114 mg, 61%), MS: m/e=459.3/460.2 (M+H⁺).

Example 8 rac-N-trans(4-{2-[4-(4-Fluoro-benzoyl)-piperidin-1-yl]-ethyl}-cyclohexyl)-2-trans (3-methoxy-cyclopentyl)-acetamide

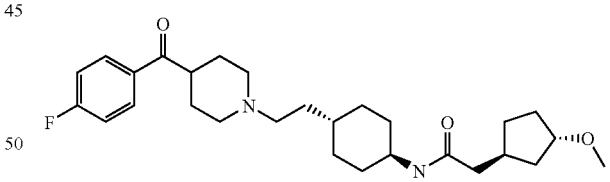

Step 1: rac-trans (3-Methoxy-cyclopentyl)-acetic acid methyl ester

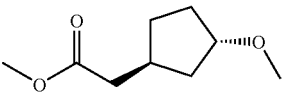

The title compound was prepared in accordance with the general method of example 2, step 3 from rac-trans-(3-hydroxy-cyclopentyl)-acetic acid methyl ester (Example 7, step 1).

Step 2: rac-N-trans (4-{2-[4-(4-Fluoro-benzoyl)-piperidin-1-yl]-ethyl}-cyclohexyl)-2-trans (3-methoxy-cyclopentyl)-acetamide The title compound, MS: m/e=473.2/474.1 (M+H⁺), was prepared in accordance with the general method of example 7, step 2 from Trans-{1-[2-(4-amino-cyclohexyl)-ethyl]-piperidin-4-yl}-(4-fluoro-phenyl)-methanone hydrochloride (intermediate F) and rac-Trans (3-methoxy-cyclopentyl)-acetic acid methyl ester.

Example 9 rac-N-trans (4-{2-[4-(4-Fluoro-benzoyl)-piperidin-1-yl]-ethyl}-cyclohexyl)-2-cis (3-methoxy-cyclopentyl)-acetamide

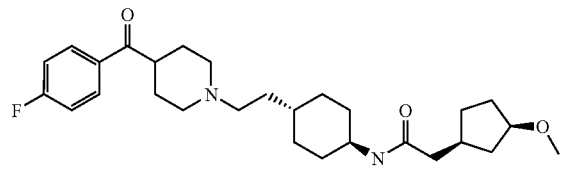

Step 1: rac-cis (3-Methoxy-cyclopentyl)-acetic acid methyl ester

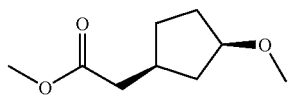

The title compound was prepared in accordance with the general method of example 2, step 3 from rac-cis (3-hydroxy-cyclopentyl)-acetic acid methyl ester (Example 6, step 1).

Step 2: rac-N-trans-(4-{2-[4-(4-Fluoro-benzoyl)-piperidin-1-yl]-ethyl}-cyclohexyl)-2-cis (3-methoxy-cyclopentyl)-acetamide The title compound, MS: m/e=473.2/474.1 (M+H⁺), was prepared in accordance with the general method of example 7, step 2 from trans-{1-[2-(4-amino-cyclohexyl)-ethyl]-piperidin-4-yl}-(4-fluoro-phenyl)-methanone hydrochloride (Example A) and rac-cis (3-methoxy-cyclopentyl)-acetic acid methyl ester.

Example 10

N-trans (4-{2-[4-(4-Fluoro-benzoyl)-piperidin-1-yl]-ethyl}-cyclohexyl)-2-((1S,3R)-3-methoxy-cyclopentyl)-acetamide or N-trans (4-{2-[4-(4-fluoro-benzoyl)-piperidin-1-yl]-ethyl}-cyclohexyl)-2-((1R,3S)-3-methoxy-cyclopentyl)-acetamide

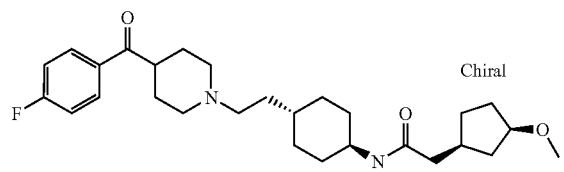

The title compound was obtained from separation using a chiral column (chiralpak AD) of rac-N-trans-(4-{2-[4-(4-fluoro-benzoyl)-piperidin-1-yl]-ethyl}-cyclohexyl)-2-cis-(3-methoxy-cyclopentyl)-acetamide (Example 9) MS (m/e): 473.3/474.3 (M+H⁺).

Example 11

N-trans (4-{2-[4-(4-Fluoro-benzoyl)-piperidin-1-yl]-ethyl}-cyclohexyl)-2-((1R,3S)-3-methoxy-cyclopentyl)-acetamide or N-trans (4-{2-[4-(4-fluoro-benzoyl)-piperidin-1-yl]-ethyl}-cyclohexyl)-2-((1S,3R)-3-methoxy-cyclopentyl)-acetamide

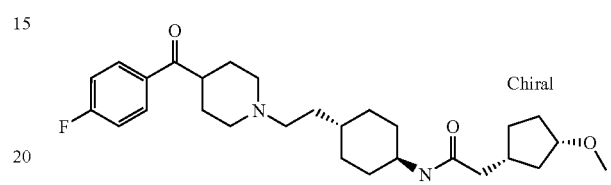

The title compound was obtained from separation using a chiral column (chiralpak AD) of rac-N-trans-(4-{2-[4-(4-fluoro-benzoyl)-piperidin-1-yl]-ethyl}-cyclohexyl)-2-cis-(3-methoxy-cyclopentyl)-acetamide (Example 9) MS (m/e): 473.3/474.3 (M+H⁺).

Example 12

2-(1,4-Dioxa-spiro[4.5]dec-8-yl)-N-trans (4-{2-[4-(4-fluoro-benzoyl)-piperidin-1-yl]-ethyl}-cyclohexyl)-acetamide

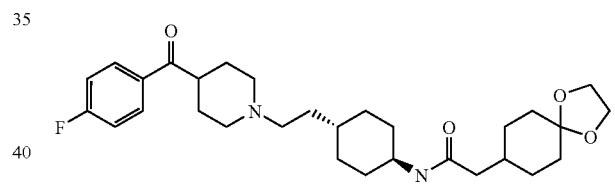

Step 1: (1,4-Dioxa-spiro[4.5]dec-8-ylidene)-acetic acid ethyl ester

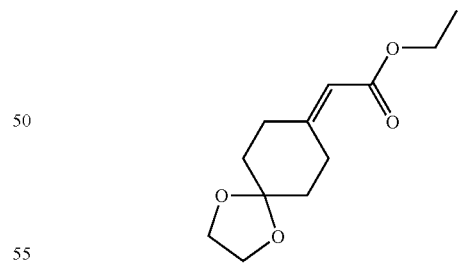

Triethyl phosphonoacetate (1.14 ml, 7.04 mmol) was dissolved in 15 ml THF and cooled to 0-5° C. Sodium hydride (310 mg, 7.04 mmol, 55%) was added and the reaction mixture stirred for 1 hour at 0-5° C. 1,4-Cyclohexanedione (1.0 g, 6.40 mmol) dissolved in 10 ml THF was added drop wise and stirred for 16 hours at room temperature. The reaction mixture was quenched with saturated NaHCO3-solution and extracted two times with ethyl acetate. The organic extracts were washed with brine, dried with sodium sulfate, filtered and evaporated. The crude product was purified by flash chromatography on silica gel (heptane/ethyl acetate 90:10→0:100 gradient). The desired compound was obtained as a colourless liquid (1.10 g, 76%), MS: m/e=227.2 (M+H⁺).

Step 2: (1,4-Dioxa-spiro[4.5]dec-8-yl)-acetic acid ethyl ester

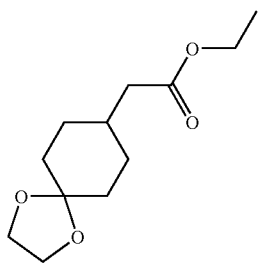

(1,4-Dioxa-spiro[4.5]dec-8-ylidene)-acetic acid ethyl ester (1.10 g, 4.86 mmol) was dissolved in 30 ml ethyl acetate and stirred with 110 mg Pd/C 10% under hydrogen atmosphere for 4 hours. The catalyst was filtered off and the solvent evaporated. The crude product (1.08 g, 97%) [MS: m/e=229.3 (M+H$^+$)] was obtained as a colourless liquid and used without any further purification for the next step.

Step 3: 2-(1,4-Dioxa-spiro[4.5]dec-8-yl)-N-trans-(4-{2-[4-(4-fluoro-benzoyl)-piperidin-1-yl]-ethyl}-cyclohexyl)-acetamide The title compound, MS: m/e=515.4/516.4 (M+H$^+$), was prepared in accordance with the general method of example 7, step 2 from trans-{1-[2-(4-amino-cyclohexyl)-ethyl]-piperidin-4-yl}-(4-fluoro-phenyl)-methanone hydrochloride (Example A) and (1,4-dioxa-spiro[4.5]dec-8-yl)-acetic acid ethyl ester.

Example 13

Trans-2-(4-Ethoxy-cyclohexyl)-N-trans (4-{2-[4-(4-fluoro-benzoyl)-piperidin-1-yl]-ethyl}-cyclohexyl)-acetamide

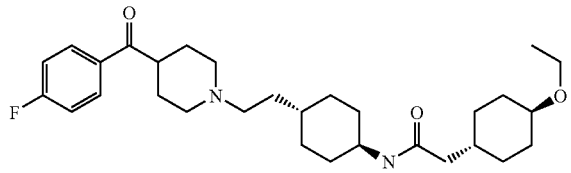

Step 1: Trans-(4-ethoxy-cyclohexyl)-acetic acid methyl ester

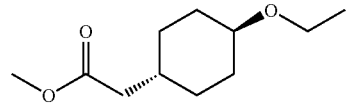

The title compound was prepared in accordance with the general method of example 2, step 1, step 2 and step 3 by using iodoethane instead of iodomethane.

Step 2: Trans-2-(4-Ethoxy-cyclohexyl)-N-trans-(4-{2-[4-(4-fluoro-benzoyl)-piperidin-1-yl]-ethyl}-cyclohexyl)-acetamide The title compound, MS: m/e=501.4/502.4 (M+H$^+$), was prepared in accordance with the general method of example 1, step 2 from Trans-{1-[2-(4-amino-cyclohexyl)-ethyl]-piperidin-4-yl}-(4-fluoro-phenyl)-methanone hydrochloride (intermediate F) and Trans-(4-Ethoxy-cyclohexyl)-acetic acid methyl ester.

Example 14

N-trans (4-{2-[4-(4-Fluoro-benzoyl)-piperidin-1-yl]-ethyl}-cyclohexyl)-2-((1S,3S)-3-methoxy-cyclopentyl)-acetamide or N-trans (4-{2-[4-(4-fluoro-benzoyl)-piperidin-1-yl]-ethyl}-cyclohexyl)-2-((1R,3R)-3-methoxy-cyclopentyl)-acetamide

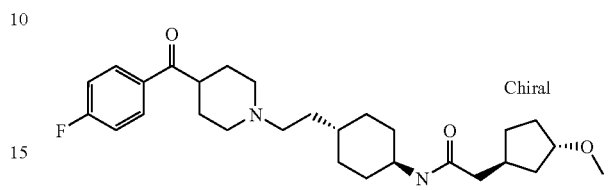

The title compound was obtained from separation using a chiral column (chiralpak AD) of rac-N-trans-(4-{2-[4-(4-fluoro-benzoyl)-piperidin-1-yl]-ethyl}-cyclohexyl)-2-trans (3-methoxy-cyclopentyl)-acetamide (Example 8) MS (m/e): 473.2/474.2 (M+H$^+$).

Example 15

N-trans (4-{2-[4-(4-Fluoro-benzoyl)-piperidin-1-yl]-ethyl}-cyclohexyl)-2-((1R,3R)-3-methoxy-cyclopentyl)-acetamide or N-trans (4-{2-[4-(4-fluoro-benzoyl)-piperidin-1-yl]-ethyl}-cyclohexyl)-2-((1S,3S)-3-methoxy-cyclopentyl)-acetamide

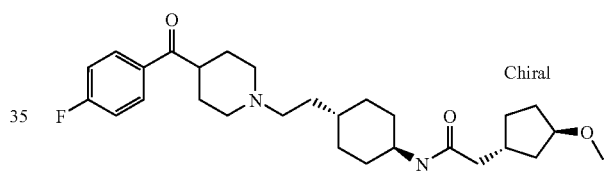

The title compound was obtained from separation using a chiral column (chiralpak AD) of rac-N-trans-(4-{2-[4-(4-fluoro-benzoyl)-piperidin-1-yl]-ethyl}-cyclohexyl)-2-trans-(3-methoxy-cyclopentyl)-acetamide (Example 8) MS (m/e): 473.2/474.2 (M+H$^+$).

Example 16

N-trans (4-{2-[4-(4-Fluoro-benzoyl)-piperidin-1-yl]-ethyl}-cyclohexyl)-2-((1R,3R)-3-methoxy-cyclohexyl)-acetamide or N-trans (4-{2-[4-(4-fluoro-benzoyl)-piperidin-1-yl]-ethyl}-cyclohexyl)-2-((1S,3S)-3-methoxy-cyclohexyl)-acetamide

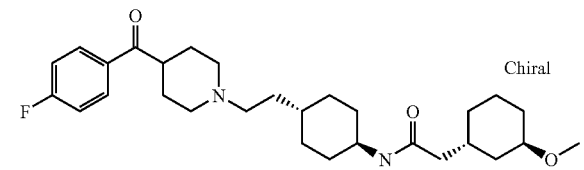

Step 1: (3-Oxo-cyclohexyl)-acetic acid methyl ester

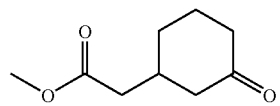

rac-cis-(3-Hydroxy-cyclohexyl)-acetic acid methyl ester (500 mg, 2.90 mmol) (Example 5, step 1) was dissolved in 2 ml dichloromethane and tetrapropylammonium perruthenate [TPAP] (102 mg, 0.29 mmol) and 4-methylmorpholine oxide monohydrate (590 mg, 4.35 mmol) were added. The reaction mixture was stirred for 16 hours at room temperature, filtered over dicalite and evaporated to dryness. The residue was purified by flash chromatography on silica gel (heptane/ethyl acetate 100:0→50:50 gradient). The desired compound was obtained as a light yellow liquid (240 mg, 48%).

Step 2: rac (3-Hydroxy-cyclohexyl)-acetic acid methyl ester

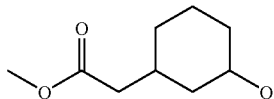

(3-Oxo-cyclohexyl)-acetic acid methyl ester (240 mg, 1.39 mmol) was dissolved in 5 ml THF and 5 ml ethanol and cooled to 0-5° C. Sodium borohydride (79 mg, 2.09 mmol) was added and the reaction mixture was stirred at room temperature for 1 hour. The reaction mixture was quenched with saturated NaHCO3-solution and extracted three times with ethyl acetate. The organic extracts were washed with brine, dried with sodium sulfate, filtered and evaporated. The crude product (240 mg, 100%) was obtained as a light yellow oil and used without any further purification for the next step.

Step 3: rac(3-Methoxy-cyclohexyl)-acetic acid methyl ester

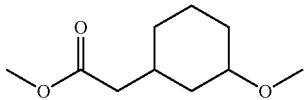

The title compound was prepared in accordance with the general method of example 2, step 3 from (3-hydroxy-cyclohexyl)-acetic acid methyl ester.

Step 4: rac-N-trans (4-{2-[4-(4-Fluoro-benzoyl)-piperidin-1-yl]-ethyl}-cyclohexyl)-2-(3-methoxy-cyclohexyl)-acetamide

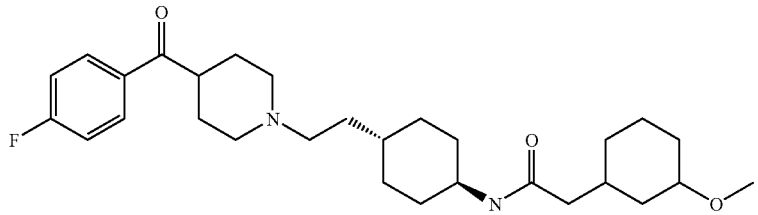

The title compound, MS: m/e=487.2/488.3 (M+H$^+$), was prepared in accordance with the general method of example 1, step 2 from trans-{1-[2-(4-amino-cyclohexyl)-ethyl]-piperidin-4-yl}-(4-fluoro-phenyl)-methanone hydrochloride (intermediate F) and (3-methoxy-cyclohexyl)-acetic acid methyl ester.

Step 5: N-trans (4-{2-[4-(4-Fluoro-benzoyl)-piperidin-1-yl]-ethyl}-cyclohexyl)-2-((1R,3R)-3-methoxy-cyclohexyl)-acetamide or N-trans(4-{2-[4-(4-fluoro-benzoyl)-piperidin-1-yl]-ethyl}-cyclohexyl)-2-((1S,3S)-3-methoxy-cyclohexyl)-acetamide The title compound was obtained from separation using a chiral column (chiralpak AD) of trans-N-(4-{2-[4-(4-fluoro-benzoyl)-piperidin-1-yl]-ethyl}-cyclohexyl)-2-(3-methoxy-cyclohexyl)-acetamide MS (m/e): 487.2/488.3 (M+H$^+$).
Note: cis analog was prepared as major compound as described on example 5.

Example 17 rac-N-Trans (4-{2-[4-(4-Fluoro-benzoyl)-piperidin-1-yl]-ethyl}-cyclohexyl)-2-[4-(tetrahydro-furan-3-yloxy)-cyclohexyl]-acetamide

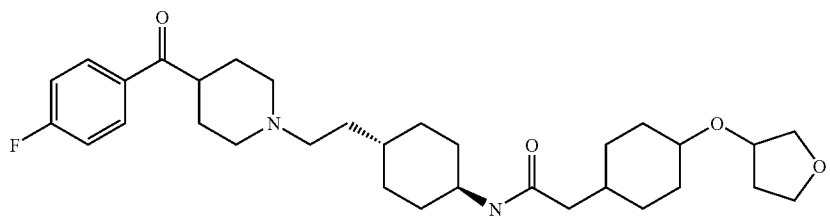

Step 1: 3-(4-Benzyloxy-phenoxy)-tetrahydro-furan

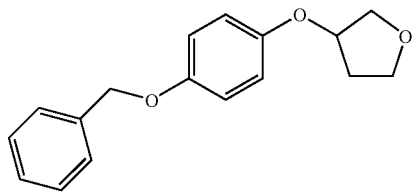

The title compound can be prepared in accordance with literature *Tetrahedron Letters,* 2003, 44 (18), p. 3609 from 4-benzyloxyphenol and 3-hydroxytetrahydrofuran.

Step 2: 4-(Tetrahydro-furan-3-yloxy)-phenol

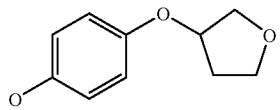

3-(4-Benzyloxy-phenoxy)-tetrahydro-furan (1.80 g, 6.66 mmol) was dissolved in 30 ml ethyl acetate and stirred with 200 mg Pd/C 10% under hydrogen atmosphere for 16 hours. The catalyst was filtered off and the solvent evaporated. The residue was purified by flash chromatography on silica gel (heptane/ethyl acetate 100:0→20:80 gradient). The desired compound was obtained as a light brown solid (900 mg, 75%) MS (m/e): 179.1 (M–H$^+$).

Step 3: 4-(Tetrahydro-furan-3-yloxy)-cyclohexanol

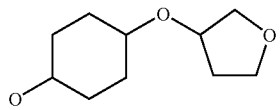

4-(Tetrahydro-furan-3-yloxy)-phenol (900 mg, 5.00 mmol) was dissolved in 25 ml 0.4N NaOH and stirred with 500 mg Rh/C 5% under hydrogen atmosphere at 60° C. and 4 bar pressure for 3 hours. The catalyst was filtered off and the clear solution acidified with conc. H$_2$SO$_4$ to pH 1. The aqueous layer was saturated with NaCl and extracted two times with dichloromethane. The organic extracts were dried with sodium sulfate, filtered and evaporated. The crude product (800 mg, 86%) was obtained as a light brown liquid and used without any further purification for the next step.

Step 4: 4-(Tetrahydro-furan-3-yloxy)-cyclohexanone

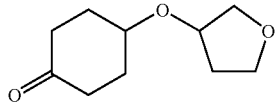

The title compound was prepared in accordance with the general method of example 16, step 1 from 4-(tetrahydro-furan-3-yloxy)-cyclohexanol.

Step 5: rac-[4-(Tetrahydro-furan-3-yloxy)-cyclohexyl]-acetic acid methyl ester

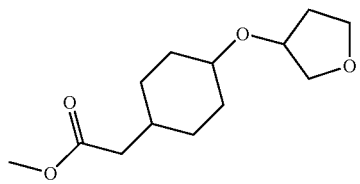

The title compound was prepared in accordance with the general method of example 12, step 1 and step 2 from 4-(tetrahydro-furan-3-yloxy)-cyclohexanone and trimethylphosphone acetate.

Step 6: rac-N-trans-(4-{2-[4-(4-Fluoro-benzoyl)-piperidin-1-yl]-ethyl}-cyclohexyl)-2-[4-(tetrahydro-furan-3-yloxy)-cyclohexyl]-acetamide The title compound, MS: m/e=543.6/544.5 (M+H$^+$), was prepared in accordance with the general method of example 1, step 2 from trans-{1-[2-(4-amino-cyclohexyl)-ethyl]-piperidin-4-yl}-(4-fluoro-phenyl)-methanone hydrochloride (intermediate F) and [4-(tetrahydro-furan-3-yloxy)-cyclohexyl]-acetic acid methyl ester.

Example 18 rac-2-(trans-3-Ethoxy-cyclopentyl)-N-trans-(4-{2-[4-(4-fluoro-benzoyl)-piperidin-1-yl]-ethyl}-cyclohexyl)-acetamide

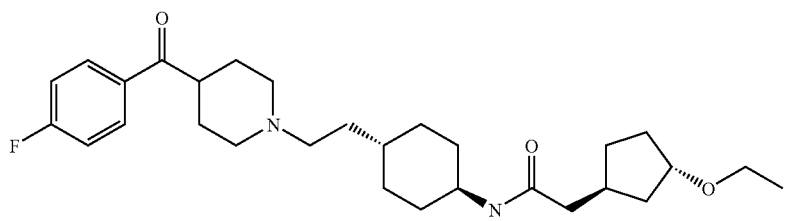

Step 1: rac-(trans-3-Ethoxy-cyclopentyl)-acetic acid methyl ester

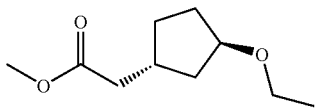

The title compound was prepared in accordance with the general method of example 8, step 1 by using iodoethane instead of iodomethane.

Step 2: rac-2-(trans-3-Ethoxy-cyclopentyl)-N-trans-(4-{2-[4-(4-fluoro-benzoyl)-piperidin-1-yl]-ethyl}-cyclohexyl)-acetamide The title compound, MS: m/e=487.5/488.4 (M+H$^+$), was prepared in accordance with the general method of example 1, step 2 from trans-{1-[2-(4-amino-cyclohexyl)-ethyl]-piperidin-4-yl}-(4-fluoro-phenyl)-methanone hydrochloride (intermediate F) and rac-(trans-3-ethoxy-cyclopentyl)-acetic acid methyl ester.

Example 19

N-trans (4-{2-[4-(4-Fluoro-benzoyl)-piperidin-1-yl]-ethyl}-cyclohexyl)-2-cis/trans (3-hydroxymethyl-cyclobutyl)-acetamide

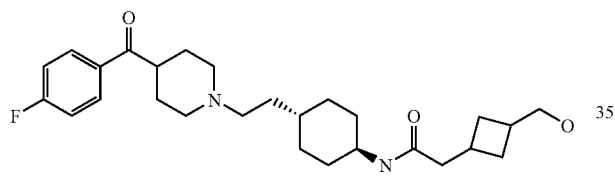

Step 1: 3-Benzyloxymethyl-cyclobutanone

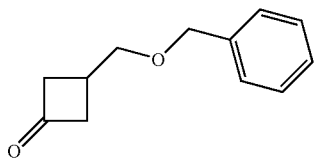

The title compound can be prepared in accordance with the literature in the patent WO2006063281.

Step 2: cis/trans (3-Hydroxymethyl-cyclobutyl)-acetic acid methyl ester

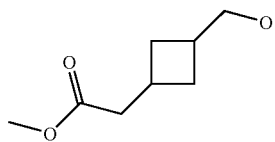

The title compound was prepared in accordance with the general method of example 12, step 1 and step 2 from 3-benzyloxymethyl-cyclobutanone and trimethylphosphone acetate.

Step 3: N-trans (4-{2-[4-(4-Fluoro-benzoyl)-piperidin-1-yl]-ethyl}-cyclohexyl)-2-cis/trans (3-hydroxymethyl-cyclobutyl)-acetamide The title compound, MS: m/e=459.4 (M+H$^+$), was prepared in accordance with the general method of example 1, step 2 from trans-{1-[2-(4-amino-cyclohexyl)-ethyl]-piperidin-4-yl}-(4-fluoro-phenyl)-methanone hydrochloride (intermediate F) and cis/trans (3-hydroxymethyl-cyclobutyl)-acetic acid methyl ester.

Example 20

N-trans(4-{2-[4-(4-Fluoro-benzoyl)-piperidin-1-yl]-ethyl}-cyclohexyl)-2-cis/trans (3-methoxymethyl-cyclobutyl)-acetamide

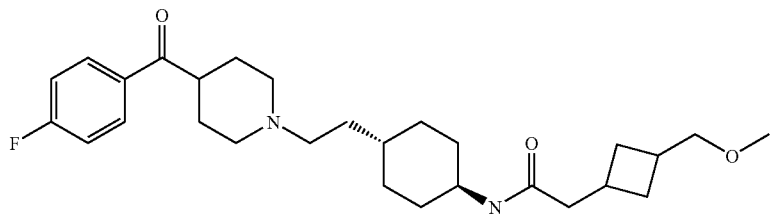

Step 1: cis/trans (3-Methoxymethyl-cyclobutyl)-acetic acid methyl ester

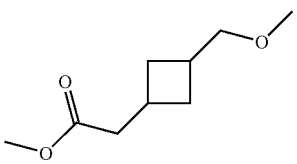

The title compound was prepared in accordance with the general method of example 8, step 1 from cis/trans (3-hydroxymethyl-cyclobutyl)-acetic acid methyl ester (Example 19, step 2).

Step 2: N-trans (4-{2-[4-(4-Fluoro-benzoyl)-piperidin-1-yl]-ethyl}-cyclohexyl)-2-cis/trans (3-methoxymethyl-cyclobutyl)-acetamide The title compound, MS: m/e=473.3 (M+H+), was prepared in accordance with the general method of example 1, step 2 from trans-{1-[2-(4-amino-cyclohexyl)-ethyl]-piperidin-4-yl}-(4-fluoro-phenyl)-methanone hydrochloride (intermediate C) and Cis/Trans (3-methoxymethyl-cyclobutyl)-acetic acid methyl ester.

Example 21

N-trans (4-{2-[4-(4-Fluoro-benzoyl)-piperidin-1-yl]-ethyl}-cyclohexyl)-2-trans (4-methoxymethyl-cyclohexyl)-acetamide

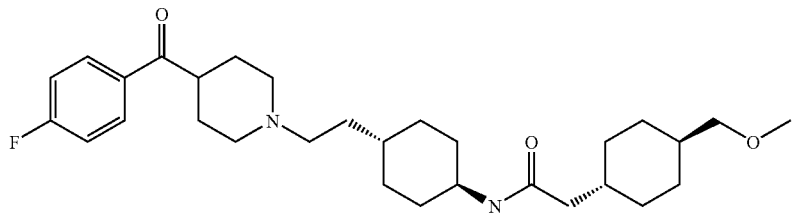

Step 1:
8-Methoxymethyl-1,4-dioxa-spiro[4.5]decane

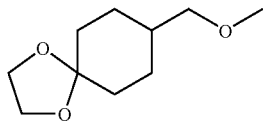

1,4-Dioxaspiro[4.5]decane-8-methanol (2 g, 1 mmol) (commercial available or prepared as in Bioorganic & Medicinal Chemistry, 13(23), 6309-6323; 2005) is methylated using MeI (1.81 mL, 29 mmol) and NaH (0.813 g, 20 mmol) in tetrahydrofuran to obtain after 2 hours of stirring at room temperature 1.4 g (7.8 mmol) of the desired compound. MS (m/e): 187.3 (M+H+).

Step 2: (4-Methoxymethyl-cyclohexylidene)-acetic acid methyl ester

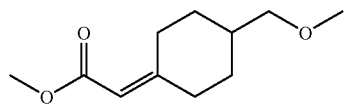

4-Methoxymethyl-cyclohexanone was obtained by treatment of 8-methoxymethyl-1,4-dioxa-spiro[4.5]decane (1.45 g, 8 mmol) with HCl 1N (15.6 mL, 16 mmol) in acetone (35 ml). Acetone was removed and the product was extracted with dichloromethane. The crude 4-methoxymethyl-cyclohexanone was solved in 1 ml of dimethoxyethane and added into a mixture previously prepared by adding n-BuLi (3.54 mL, 6 mmol) to methyl diethylphosphonoacetate (1.03 g, 5 mmol) in DME by stirring for 10 minutes at 0° C. After 2 hours TLC indicated formation of the (4-Methoxymethyl-cyclohexylidene)-acetic acid methyl ester (0.552 g, 2.7 mmol). MS (m/e): 199.1 (M+H+).

Step 3: cis/trans (4-Methoxymethyl-cyclohexyl)-acetic acid methyl ester

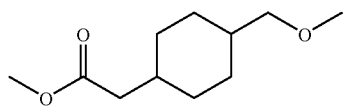

Prepared from (4-Methoxymethyl-cyclohexylidene)-acetic acid methyl ester (0.550 g, 3 mmol) by hydrogenation using Pd/C (10%) (0.295 g, 0.3 mmol) in ethylacetate (15 ml). 1/3 cis/trans mixture.

Step 4: N-trans-(4-{2-[4-(4-Fluoro-benzoyl)-piperidin-1-yl]-ethyl}-cyclohexyl)-2-trans (4-methoxymethyl-cyclohexyl)-acetamide The title compound, MS: m/e=501.3 (M+H+), was prepared in accordance with the general method of example 1, step 2 from trans-{1-[2-(4-amino-cyclohexyl)-ethyl]-piperidin-4-yl}-(4-fluoro-phenyl)-methanone hydrochloride (intermediate F) and (4-methoxymethyl-cyclohexyl)-acetic acid methyl ester. The pure trans diastereoisomer was obtained by crystallization using diisopropylether.

Example 22

N-trans (4-{2-[4-(4-Fluoro-benzoyl)-piperidin-1-yl]-ethyl}-cyclohexyl)-2-(4-cis/trans-hydroxy-4-methyl-cyclohexyl)-acetamide

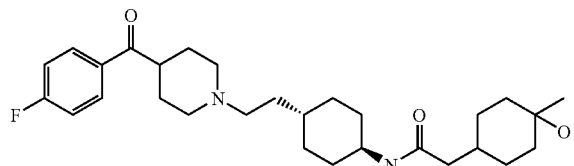

Step 1: (4-Oxo-cyclohexyl)-acetic acid

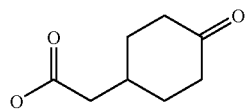

Prepared from LiOH hydrolysis of (4-Oxo-Cyclohexyl)-acetic acid methyl ester (commercial available).

Step 2: (4-Hydroxy-4-methyl-cyclohexyl)-acetic acid

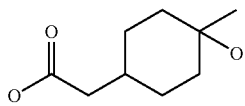

Prepared using an excess of MeMgBr (26 mmol) in THF (20 ml) with (4-Oxo-cyclohexyl)-acetic acid (13 mmol) as described on Journal of American Society 93 (1), 1971, 121-129.

Step 3: N-trans (4-{2-[4-(4-Fluoro-benzoyl)-piperidin-1-yl]-ethyl}-cyclohexyl)-2-(4-cis/trans-hydroxy-4-methyl-cyclohexyl)-acetamide The title compound, MS: m/e=487.5 (M+H$^+$), was prepared in accordance with the general method of example 4, step 2 from Trans{1-[2-(4-amino-cyclohexyl)-ethyl]-piperidin-4-yl}-(4-fluoro-phenyl)-methanone hydrochloride (intermediate F) and (4-hydroxy-4-methyl-cyclohexyl)-acetic acid.

Example 23

N-trans (4-{2-[4-(4-Fluoro-benzoyl)-piperidin-1-yl]-ethyl}-cyclohexyl)-2-(4-trans-hydroxy-4-methyl-cyclohexyl)-acetamide or N-trans (4-{2-[4-(4-fluoro-benzoyl)-piperidin-1-yl]-ethyl}-cyclohexyl)-2-(4-cis-hydroxy-4-methyl-cyclohexyl)-acetamide

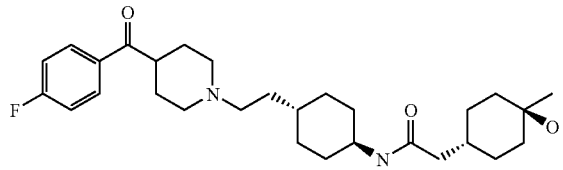

The title compound was obtained from separation using a chiral column (chiralpak AD) of N-trans-(4-{2-[4-(4-fluoro-benzoyl)-piperidin-1-yl]-ethyl}-cyclohexyl)-2-(4-cis/trans-hydroxy-4-methyl-cyclohexyl)-acetamide (Example 22) MS (m/e): 487.5 (M+H$^+$).

Example 24

N-trans (4-{2-[4-(4-Fluoro-benzoyl)-piperidin-1-yl]-ethyl}-cyclohexyl)-2-(4-cis-hydroxy-4-methyl-cyclohexyl)-acetamide or N-trans (4-{2-[4-(4-fluoro-benzoyl)-piperidin-1-yl]-ethyl}-cyclohexyl)-2-(4-trans-hydroxy-4-methyl-cyclohexyl)-acetamide

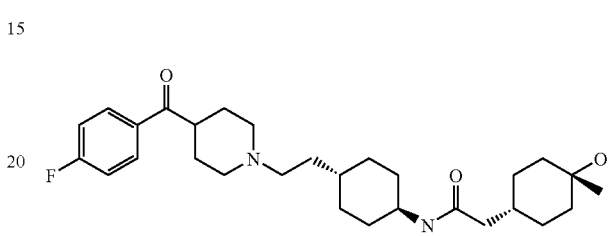

The title compound was obtained from separation using a chiral column (chiralpak AD) of N-trans-(4-{2-[4-(4-fluoro-benzoyl)-piperidin-1-yl]-ethyl}-cyclohexyl)-2-(4-cis/trans-hydroxy-4-methyl-cyclohexyl)-acetamide (Example 22) MS (m/e): 487.5 (M+H$^+$).

Example 25

N-trans (4-{2-[4-(4-Fluoro-benzoyl)-piperidin-1-yl]-ethyl}-cyclohexyl)-2-trans (3-methoxymethyl-cyclobutyl)-acetamide

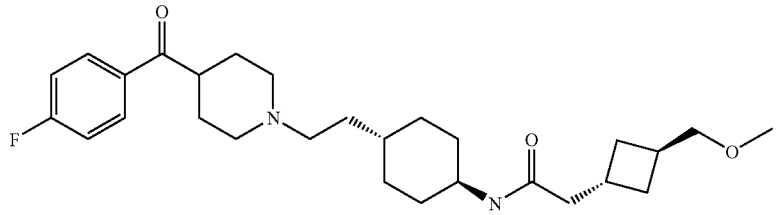

The title compound was obtained from separation using a chiral column (chiralpak AD) of N-trans (4-{2-[4-(4-fluoro-benzoyl)-piperidin-1-yl]-ethyl}-cyclohexyl)-2-cis/trans (3-methoxymethyl-cyclobutyl)-acetamide (Example 20) MS (m/e): 473.2 (M+H$^+$).

Example 26

N-trans (4-{2-[4-(4-Fluoro-benzoyl)-piperidin-1-yl]-ethyl}-cyclohexyl)-2-cis (3-methoxymethyl-cyclobutyl)-acetamide

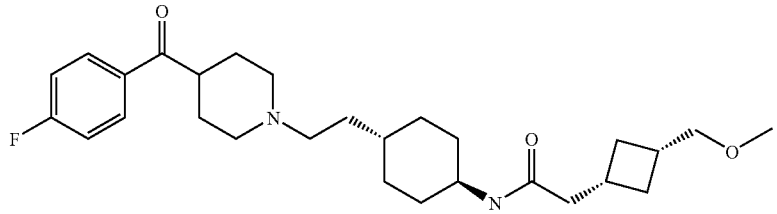

The title compound was obtained from separation using a chiral column (chiralpak AD) of N-trans (4-{2-[4-(4-fluoro-benzoyl)-piperidin-1-yl]-ethyl}-cyclohexyl)-2-cis/trans (3-methoxymethyl-cyclobutyl)-acetamide (Example 20) MS (m/e): 473.2 (M+H$^+$).

Example 27

2-trans (4-Acetylamino-cyclohexyl)-N-trans-(4-{2-[4-(4-fluoro-benzoyl)-piperidin-1-yl]-ethyl}-cyclohexyl)-acetamide

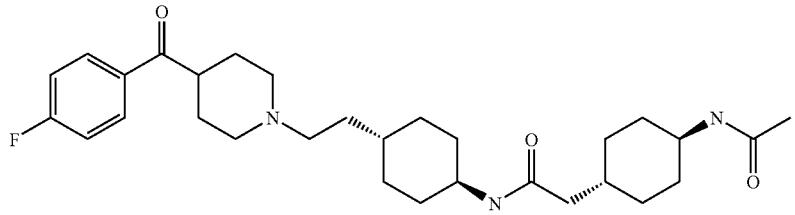

Step 1: trans-(4-Acetylamino-cyclohexyl)-acetic acid ethyl ester

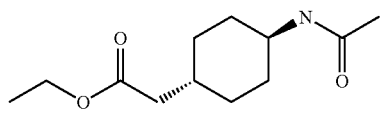

Trans-(4-Amino-cyclohexyl)-acetic acid ethyl ester hydrochloride (1.0 g, 4.51 mmol) (Example A, step 2) was dissolved in dichloromethane and triethylamine (1.89 ml, 13.5 mmol) was added. Acetyl chloride (0.35 ml, 4.96 mmol) was added drop wise and the reaction mixture stirred for 5 hours at room temperature. The reaction mixture was quenched with saturated NaHCO3-solution and extracted with dichloromethane. The organic extracts were washed with brine, dried with sodium sulfate, filtered and evaporated. The crude product (804 mg, 78%) [MS: m/e=228.3/229.3 (M+H$^+$)] was obtained as a white solid and used without any further purification for the next step.

Step 2: 2-trans (4-Acetylamino-cyclohexyl)-N-trans-(4-{2-[4-(4-fluoro-benzoyl)-piperidin-1-yl]-ethyl}-cyclohexyl)-acetamide The title compound, MS: m/e=514.3 (M+H$^+$), was prepared in accordance with the general method of example 7, step 2 from trans-{1-[2-(4-amino-cyclohexyl)-ethyl]-piperidin-4-yl}-(4-fluoro-phenyl)-methanone hydrochloride (intermediate F) and trans-(4-Acetylamino-cyclohexyl)-acetic acid ethyl ester.

Example 28 rac-N-trans (4-{2-[4-(4-Fluoro-benzoyl)-piperidin-1-yl]-ethyl}-cyclohexyl)-2-(3-methoxymethyl-cyclopentyl)-acetamide

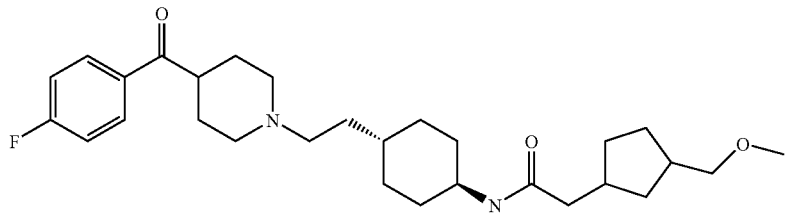

Step 1: (1,4-Dioxa-spiro[4.5]non-7-yl)-methanol

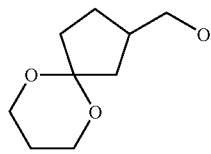

The title compound can be prepared in two steps from 3-oxo-1-cyclopentanecarboxylic ethyl ester in benzene containing propylene glycol to obtain the 6,10-Dioxa-spiro[4.5]decane-2-carboxylic acid ethyl ester. Reduction of the ester to acid was performed using LiAlH4 as similarly described on *Synthetic Communications*, 18(15), 1988, 1883-1890.

Step 2: rac-(3-Methoxymethyl-cyclopentyl)-acetic acid methyl ester

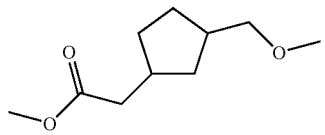

The title compound was prepared in accordance with the general method of example 21, step 1, step 2 and step 3 from (1,4-dioxa-spiro[4.4]non-7-yl)-methanol. MS: m/e=187.4 (M+H$^+$)

Step 3: rac-N-trans (4-{2-[4-(4-Fluoro-benzoyl)-piperidin-1-yl]-ethyl}-cyclohexyl)-2-(3-methoxymethyl-cyclopentyl)-acetamide The title compound, MS: m/e=487.4 (M+H$^+$), was prepared in accordance with the general method of example 1, step 2 from trans-{1-[2-(4-amino-cyclohexyl)-ethyl]-piperidin-4-yl}-(4-fluoro-phenyl)-methanone hydrochloride (intermediate F) and rac-(3-methoxymethyl-cyclopentyl)-acetic acid methyl ester.

Example 29 rac-N-trans (4-{2-[4-(4-Fluoro-benzoyl)-piperidin-1-yl]-ethyl}-cyclohexyl)-3-(4-methoxy-cyclohexyl)-propionamide

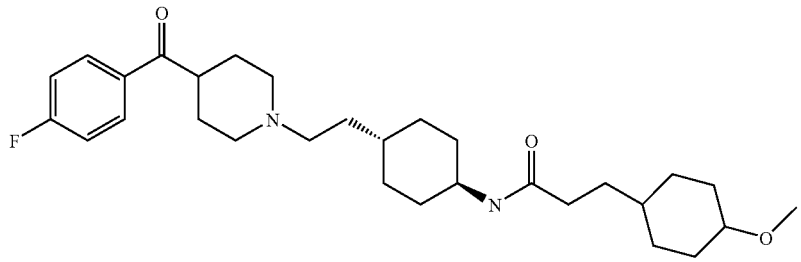

Step 1: 4-Methoxy-cyclohexanecarbaldehyde

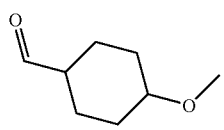

The title compound can be prepared in accordance with the literature in the patent DE3718870.

Step 2: rac-3-(4-Methoxy-cyclohexyl)-propionic acid methyl ester

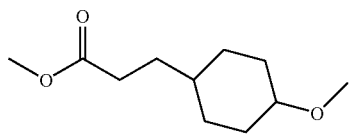

The title compound was prepared in accordance with the general method of example 12, step 1 and step 2 from 3-(4-methoxy-cyclohexyl)-propionic acid methyl ester and trimethylphosphone acetate.

Step 3: rac-N-trans-(4-{2-[4-(4-Fluoro-benzoyl)-piperidin-1-yl]-ethyl}-cyclohexyl)-3-(4-methoxy-cyclohexyl)-propionamide The title compound, MS: m/e=501.0/502.2 (M+H$^+$), was prepared in accordance with the general method of example 1, step 2 from trans-{1-[2-(4-amino-cyclohexyl)-ethyl]-piperidin-4-yl}-(4-fluoro-phenyl)-methanone hydrochloride (Example A) and rac-3-(4-methoxy-cyclohexyl)-propionic acid methyl ester.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient can be sieved and mixed with microcrystalline cellulose, and the mixture can be granulated with a solution of polyvinylpyrrolidone in water. The granulate can be mixed with sodium starch glycolate and magnesiumstearate and compressed to yield kernels of 120 or 350 mg respectively. The kernels can be lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components can be sieved, mixed, and filled into capsules of size 2.

Example C

Injection solutions can have the following composition:

| | |
|---|---|
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient can be dissolved in a warm melting of the other ingredients, and the mixture can be filled into soft gelatin capsules of appropriate size. The filled soft gelatin capsules can be treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient can be mixed with lactose, microcrystalline cellulose and sodium carboxymethyl cellulose and granulated with a mixture of polyvinylpyrrolidone in water. The granulate can be mixed with magnesium stearate and the flavoring additives and then filled into sachets.

The invention claimed is:

1. A compound of formula (I):

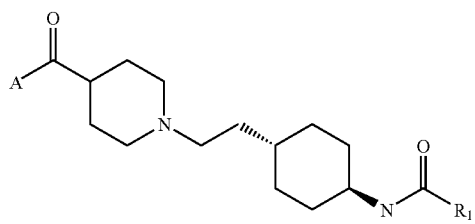

wherein
$R_1$:

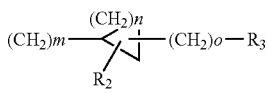

A is aryl which is optionally substituted by one to five substituents selected from the group consisting of cyano, halo, $C_{1-6}$-alkyl, $C_{1-6}$-haloalkyl and $C_{1-6}$-alkoxy;
m is 1, 2 or 3;
n is 1, 2, 3, 4 or 5;
o is 0, 1 or 2;
$R_2$ is selected from the group consisting of hydrogen, hydroxyl, $C_{1-6}$-alkyl, $C_{1-6}$-haloalkyl and $C_{1-6}$-alkoxy; and
$R_3$ is selected from the group consisting of
hydrogen, provided that $R_2$ is not hydrogen;
hydroxyl;
$C_{1-6}$-alkyl;
$C_{1-6}$-haloalkyl;
$C_{1-6}$-haloalkoxy;
oxo;
—NH(CO)—$C_{1-6}$-alkyl;
—O—$C_{1-6}$-alkyl; and
—O—$C_{3-7}$-cycloalkyl;
or a pharmaceutically acceptable salt thereof.

2. A compound of claim 1 having formula (Ia):

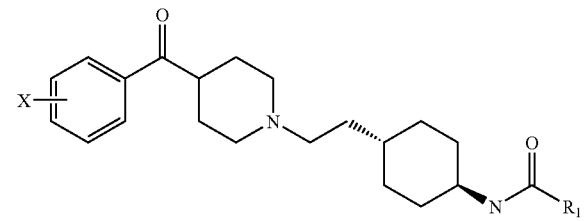

wherein
$R_1$:

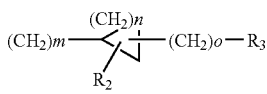

X is halo;
m is 1 or 2;
n is 2, 3 or 4;
o is 0 or 1;
$R_2$ is selected from the group consisting of hydrogen, hydroxyl, $C_{1-6}$-alkyl and $C_{1-6}$-alkoxy; and
$R_3$ is selected from the group consisting of
hydroxyl;
$C_{1-6}$-alkyl;
oxo;
—NH(CO)—$C_{1-6}$-alkyl;
—O—$C_{1-6}$-alkyl; and
—O—$C_{3-7}$-cycloalkyl;
or a pharmaceutically acceptable salt thereof.

3. A compound of claim 2:
wherein
$R_2$ is H or methyl; and
$R_3$ is hydroxyl or $C_{1-6}$-alkoxy, and $R^2$ and —$(CH_2)_o$—$R^3$ are bound to the same cycloalkyl carbon atom;
or a pharmaceutically acceptable salt thereof.

4. A compound of claim 1 having formula (Ib):

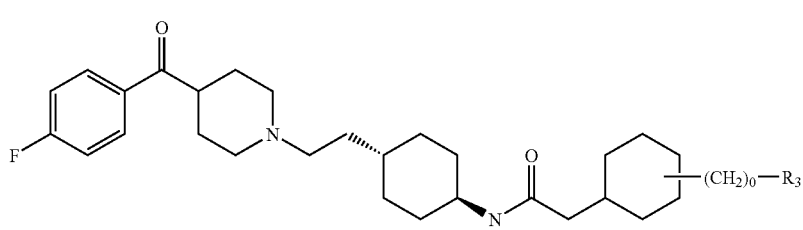

(Ib)

wherein
o is 0 or 1; and
$R_3$ is hydroxyl or $C_{1-6}$-alkoxy;
or a pharmaceutically acceptable salt thereof.

5. A compound of claim 4:
wherein o is 0;
or a pharmaceutically acceptable salt thereof.

6. A compound of formula (Ic) according to claim 1:

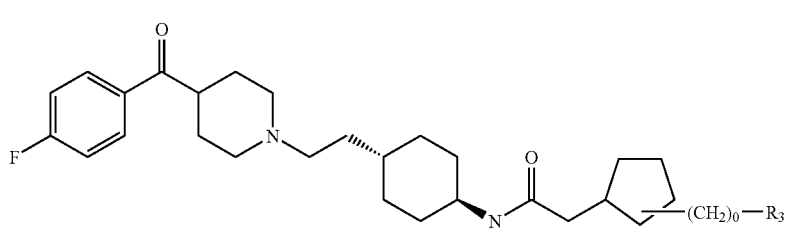

(Ic)

wherein
o is 0 or 1; and
$R_3$ is hydroxyl or $C_{1-6}$-alkoxy;
or a pharmaceutically acceptable salt thereof.

7. A compound of claim 1 having formula (Id):

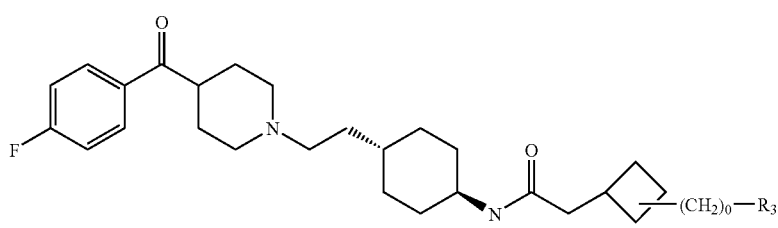

(Id)

wherein
o is 0 or 1; and
$R_3$ is hydroxyl or $C_{1-6}$-alkoxy;
or a pharmaceutically acceptable salt thereof.

8. A compound of claim 1, selected from the group consisting of:
  N-trans (4-{2-[4-(4-Fluoro-benzoyl)-piperidin-1-yl]-ethyl}-cyclohexyl)-2-cis/trans (4-hydroxy-cyclohexyl)-acetamide,
  N-trans (4-{2-[4-(4-Fluoro-benzoyl)-piperidin-1-yl]-ethyl}-cyclohexyl)-2-cis (4-methoxy-cyclohexyl)-acetamide,
  N-trans (4-{2-[4-(4-Fluoro-benzoyl)-piperidin-1-yl]-ethyl}-cyclohexyl)-2-trans (4-methoxy-cyclohexyl)-acetamide,
  rac-N-trans (4-{2-[4-(4-Fluoro-benzoyl)-piperidin-1-yl]-ethyl}-cyclohexyl)-2-cis (3-hydroxy-cyclohexyl)-acetamide,
  rac-N-trans (4-{2-[4-(4-Fluoro-benzoyl)-piperidin-1-yl]-ethyl}-cyclohexyl)-2-cis (3-methoxy-cyclohexyl)-acetamide,
  rac-N-trans (4-{2-[4-(4-Fluoro-benzoyl)-piperidin-1-yl]-ethyl}-cyclohexyl)-2-cis (3-hydroxy-cyclopentyl)-acetamide,
  rac-N-trans (4-{2-[4-(4-Fluoro-benzoyl)-piperidin-1-yl]-ethyl}-cyclohexyl)-2-trans (3-hydroxy-cyclopentyl)-acetamide,
  rac-N-trans (4-{2-[4-(4-Fluoro-benzoyl)-piperidin-1-yl]-ethyl}-cyclohexyl)-2-trans (3-methoxy-cyclopentyl)-acetamide,
  rac-N-trans (4-{2-[4-(4-Fluoro-benzoyl)-piperidin-1-yl]-ethyl}-cyclohexyl)-2-cis (3-methoxy-cyclopentyl)-acetamide, and N-trans (4-{2-[4-(4-Fluoro-benzoyl)-piperidin-1-yl]-ethyl}-cyclohexyl)-2-((1S,3R)-3-methoxy-cyclopentyl)-acetamide or N-trans-(4-{2-[4-(4-fluoro-benzoyl)-piperidin-1-yl]-ethyl}-cyclohexyl)-2-((1R,3S)-3-methoxy-cyclopentyl)-acetamide.

9. A compound of claim 1, selected from the group consisting of:
N-trans (4-{2-[4-(4-Fluoro-benzoyl)-piperidin-1-yl]-ethyl}-cyclohexyl)-2-((1R,3S)-3-methoxy-cyclopentyl)-acetamide or N-trans-(4-{2-[4-(4-fluoro-benzoyl)-piperidin-1-yl]-ethyl}-cyclohexyl)-2-((1S,3R)-3-methoxy-cyclopentyl)-acetamide,
Trans-2-(4-Ethoxy-cyclohexyl)-N-trans (4-{2-[4-(4-fluoro-benzoyl)-piperidin-1-yl]-ethyl}-cyclohexyl)-acetamide,
N-trans (4-{2-[4-(4-Fluoro-benzoyl)-piperidin-1-yl]-ethyl}-cyclohexyl)-2-((1S,3S)-3-methoxy-cyclopentyl)-acetamide or N-trans (4-{2-[4-(4-fluoro-benzoyl)-piperidin-1-yl]-ethyl}-cyclohexyl)-2-((1R,3R)-3-methoxy-cyclopentyl)-acetamide,
N-trans-(4-{2-[4-(4-Fluoro-benzoyl)-piperidin-1-yl]-ethyl}-cyclohexyl)-2-((1R,3R)-3-methoxy-cyclopentyl)-acetamide or N-trans-(4-{2-[4-(4-fluoro-benzoyl)-piperidin-1-yl]-ethyl}-cyclohexyl)-2-((1S,3S)-3-methoxy-cyclopentyl)-acetamide,
N-trans (4-{2-[4-(4-Fluoro-benzoyl)-piperidin-1-yl]-ethyl}-cyclohexyl)-2-((1R,3R)-3-methoxy-cyclohexyl)-acetamide or N-trans-(4-{2-[4-(4-fluoro-benzoyl)-piperidin-1-yl]-ethyl}-cyclohexyl)-2-((1S,3S)-3-methoxy-cyclohexyl)-acetamide,
rac-2-(trans-3-Ethoxy-cyclopentyl)-N-trans-(4-{2-[4-(4-fluoro-benzoyl)-piperidin-1-yl]-ethyl}-cyclohexyl)-acetamide,
N-trans (4-{2-[4-(4-Fluoro-benzoyl)-piperidin-1-yl]-ethyl}-cyclohexyl)-2-cis/trans (3-hydroxymethyl-cyclobutyl)-acetamide, and
N-trans (4-{2-[4-(4-Fluoro-benzoyl)-piperidin-1-yl]-ethyl}-cyclohexyl)-2-cis/trans (3-methoxymethyl-cyclobutyl)-acetamide.

10. A compound of claim 1, selected from the group consisting of:
N-trans (4-{2-[4-(4-Fluoro-benzoyl)-piperidin-1-yl]-ethyl}-cyclohexyl)-2-trans (4-methoxymethyl-cyclohexyl)-acetamide,
N-trans (4-{2-[4-(4-Fluoro-benzoyl)-piperidin-1-yl]-ethyl}-cyclohexyl)-2-(4-cis/trans-hydroxy-4-methyl-cyclohexyl)-acetamide,
N-trans (4-{2-[4-(4-Fluoro-benzoyl)-piperidin-1-yl]-ethyl}-cyclohexyl)-2-(4-trans-hydroxy-4-methyl-cyclohexyl)-acetamide or N-trans-(4-{2-[4-(4-fluoro-benzoyl)-piperidin-1-yl]-ethyl}-cyclohexyl)-2-(4-cis-hydroxy-4-methyl-cyclohexyl)-acetamide,
N-trans (4-{2-[4-(4-Fluoro-benzoyl)-piperidin-1-yl]-ethyl}-cyclohexyl)-2-(4-cis-hydroxy-4-methyl-cyclohexyl)-acetamide or N-trans-(4-{2-[4-(4-fluoro-benzoyl)-piperidin-1-yl]-ethyl}-cyclohexyl)-2-(4-trans-hydroxy-4-methyl-cyclohexyl)-acetamide,
N-trans (4-{2-[4-(4-Fluoro-benzoyl)-piperidin-1-yl]-ethyl}-cyclohexyl)-2-trans (3-methoxymethyl-cyclobutyl)-acetamide,
N-trans (4-{2-[4-(4-Fluoro-benzoyl)-piperidin-1-yl]-ethyl}-cyclohexyl)-2-cis (3-methoxymethyl-cyclobutyl)-acetamide,
2-trans (4-Acetylamino-cyclohexyl)-N-trans-(4-{2-[4-(4-fluoro-benzoyl)-piperidin-1-yl]ethyl}-cyclohexyl)-acetamide,
rac-N-trans (4-{2-[4-(4-Fluoro-benzoyl)-piperidin-1-yl]-ethyl}-cyclohexyl)-2-(3-methoxymethyl-cyclopentyl)-acetamide, and
rac-N-trans (4-{2-[4-(4-Fluoro-benzoyl)-piperidin-1-yl]-ethyl}-cyclohexyl)-3-(4-methoxy-cyclohexyl)-propionamide.

11. A pharmaceutical composition comprising a therapeutically effective amount of a compound of formula (I)

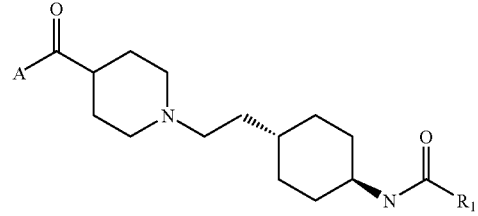

(I)

wherein
R$_1$:

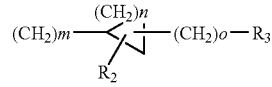

A is aryl which is optionally substituted by one to five substituents selected from the group consisting of cyano, halo, C$_{1-6}$-alkyl, C$_{1-6}$-haloalkyl and C$_{1-6}$-alkoxy;
m is 1, 2 or 3;
n is 1, 2, 3, 4 or 5;
o is 0, 1 or 2;
R$_2$ is selected from the group consisting of hydrogen, hydroxyl, C$_{1-6}$-alkyl, C$_{1-6}$-haloalkyl and C$_{1-6}$-alkoxy; and
R$_3$ is selected from the group consisting of
hydrogen, provided that R$_2$ is not hydrogen;
hydroxyl;
C$_{1-6}$-alkyl;
C$_{1-6}$-haloalkyl;
C$_{1-6}$-haloalkoxy;
oxo;
—NH(CO)—C$_{1-6}$-alkyl;
—O—C$_{1-6}$-alkyl; and
—O—C$_{3-7}$-cycloalkyl;
or a pharmaceutically acceptable salt thereof and a pharmaceutically acceptable carrier.

12. The pharmaceutical composition of claim 11, wherein the compound of formula (I) has formula (Ia)

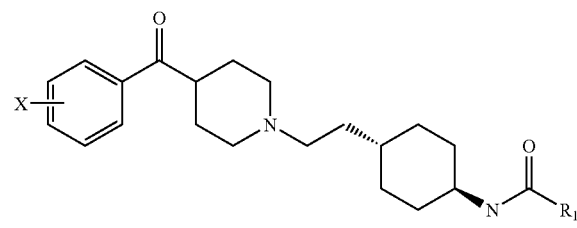

(Ia)

wherein
R$_1$:

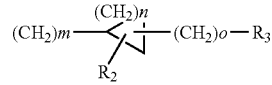

X is halo;
m is 1 or 2;
n is 2, 3 or 4;
o is 0 or 1;
R$_2$ is selected from the group consisting of hydrogen, hydroxyl, C$_{1-6}$-alkyl and C$_{1-6}$-alkoxy; and
R$_3$ is selected from the group consisting of
hydroxyl;
C$_{1-6}$-alkyl;
oxo;
—NH(CO)—C$_{1-6}$-alkyl;
—O—C$_{1-6}$-alkyl; and
—O—C$_{3-7}$-cycloalkyl;
or a pharmaceutically acceptable salt thereof.

13. The pharmaceutical composition of claim 11, wherein the compound of formula (I) has formula (Ib)

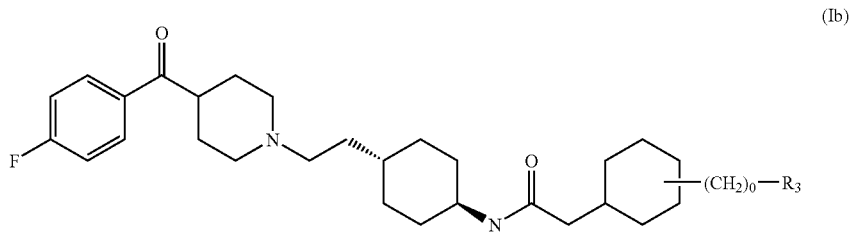

(Ib)

wherein
o is 0 or 1; and
$R_3$ is hydroxyl or $C_{1-6}$-alkoxy;
or a pharmaceutically acceptable salt thereof.

14. The pharmaceutical composition of claim 11, wherein the compound of formula (I) has formula (Ic)

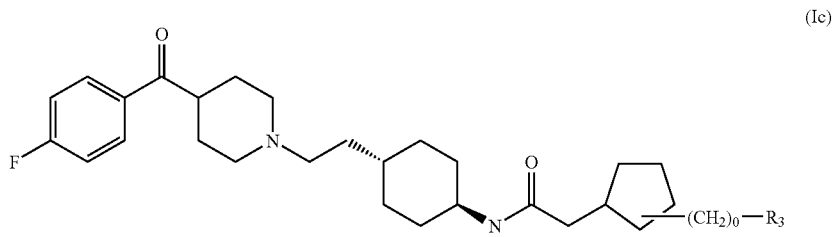

(Ic)

wherein
o is 0 or 1; and
$R_3$ is hydroxyl or $C_{1-6}$-alkoxy;
or a pharmaceutically acceptable salt thereof.

15. The pharmaceutical composition of claim 11, wherein the compound of formula (I) has formula (Id)

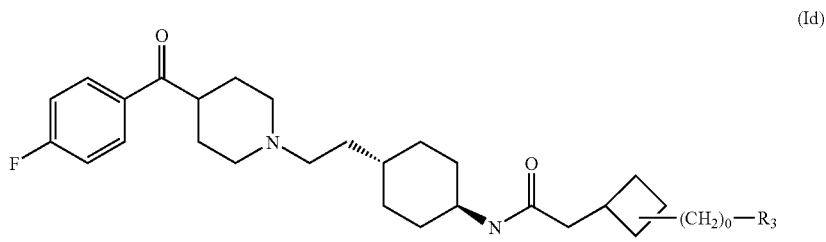

(Id)

wherein
o is 0 or 1; and
$R_3$ is hydroxyl or $C_{1-6}$-alkoxy;
or a pharmaceutically acceptable salt thereof.

* * * * *